US006936473B2

(12) United States Patent
Nanba et al.

(10) Patent No.: US 6,936,473 B2
(45) Date of Patent: Aug. 30, 2005

(54) METHOD OF PREPARING A BIOLOGICAL SAMPLE FOR QUANTIFICATION

(75) Inventors: Hiromi Nanba, Tokyo (JP); Osamu Koga, Nagasaki-Ken (JP); Masatoshi Horita, Shimabara (JP); Yoshio Ohta, Okayama (JP)

(73) Assignee: Leisure, Inc., Tokyo (JP)

( * ) Notice: Subject to any disclaimer, the term of this patent is extended or adjusted under 35 U.S.C. 154(b) by 142 days.

(21) Appl. No.: 09/995,812

(22) Filed: Nov. 29, 2001

(65) Prior Publication Data

US 2002/0153316 A1 Oct. 24, 2002

Related U.S. Application Data

(63) Continuation-in-part of application No. 09/753,715, filed on Jan. 4, 2001, now abandoned.

(30) Foreign Application Priority Data

Jan. 5, 2000 (JP) .............................................. 2000-297
Jan. 5, 2001 (JP) ....................................... 2001-000830

(51) Int. Cl.$^7$ ............................ G01N 1/00; G01N 33/48
(52) U.S. Cl. ......................... 436/174; 436/179; 436/63
(58) Field of Search .............................. 436/174, 179, 436/180, 63, 68–69

(56) References Cited

U.S. PATENT DOCUMENTS

| 4,097,237 A | * | 6/1978 | Oberhardt et al. ............. 435/2 |
| 4,683,223 A | * | 7/1987 | Trivedi ......................... 514/46 |
| 4,898,573 A | | 2/1990 | Takenaka et al. |
| 4,970,052 A | | 11/1990 | Oberhardt et al. |
| 5,135,719 A | | 8/1992 | Hillman et al. |
| 5,304,348 A | | 4/1994 | Burd et al. |
| 5,496,737 A | * | 3/1996 | Bickar .......................... 436/86 |
| 5,624,597 A | | 4/1997 | Buhl et al. |
| 5,665,238 A | | 9/1997 | Whitson et al. |
| 6,001,259 A | | 12/1999 | Whitmore |
| 6,338,967 B1 | * | 1/2002 | Bickar .......................... 436/86 |

FOREIGN PATENT DOCUMENTS

| WO | WO 91/08782 | 6/1991 |
| WO | WO 96/20402 | 7/1996 |
| WO | WO 97/29369 | 8/1997 |

* cited by examiner

Primary Examiner—Lyle A. Alexander
(74) Attorney, Agent, or Firm—Nixon Peabody LLP; Donald R. Studebaker

(57) ABSTRACT

The present invention is directed to a method of preparing a biological sample for quantification which includes an element to be quantified. A volume of biological sample is collected without quantifying the volume thereof to mix with a specified volume of an aqueous solution. Absorptivity of an indicating material in the aqueous solution is measured. Absorptivity of the indicating material in the collected biological sample mixed with the specified volume of the aqueous solution is measured. Next, a dilution ratio of the biological sample is calculated using the absorptivity of the indicating material in the specified volume of the aqueous solution and the absorptivity of the indicating material in the biological sample mixed with the specified volume of the aqueous solution. Absorptivity of the element in the biological sample mixed with the specified volume of aqueous solution is measured and a quantified value of the element in the biological sample is obtained using the measured absorptivity of the element and the calculated dilution ratio.

8 Claims, 18 Drawing Sheets

METHOD OF PREPARING A BIOLOGICAL SAMPLE FOR QUANTIFICATION

FIELD OF THE INVENTION

The present invention relates to an instrument and a method for blood separation, and in particular, an instrument and a method for separating collected blood into blood cell and blood plasma, right on the spot of collection. The present invention further relates to a preparing method of a sample for quantification used for clinical diagnosis, a method for quantifying elements to be quantified in a biological sample by using the sample for qualification prepared by said preparing method, and a container used for preparing the sample for quantification.

DESCRIPTION OF THE PRIOR ART

Generally, a blood collection is categorized into a normal blood collection where a specifically qualified person, such as a doctor, collects blood from a vein by using a syringe, and a self-blood collection where a test subject collects blood in person by pricking a finger of his or her hand with a blood collecting needle.

Conventionally the blood collected by normal blood collection system is carried to a test station as contained in an airtight container, where the blood is tested after it has been separated into blood cell and blood plasma by a centrifugal separator. On the other hand, the blood collected by self-blood collection system is carried to the test station as dried after impregnated into a filter paper, where an analyses is conducted in a way that a white part of the filter paper representative of the blood plasma is cut off at the test station and then is dissolved into a solvent, leaving a red part thereof representative of the blood cell.

In a clinical inspection, a specifically qualified person, such as a doctor, a nurse and a clinical inspection engineer or an expert engineer collects a biological sample by the blood collection or the like, prepares a sample for quantification from the collected biological sample and quantifies an element to be quantified in a biological sample.

Although in a special inspection item for a qualitative or a semi-quantitative judgment, there has been known a method where a test subject collects his/her own biological sample by himself/herself, in a general inspection item for quantification, it has been required that the test subject goes to a hospital or an inspection center where the specifically qualified person, such as a doctor, a nurse and a clinical inspection engineer or the expert engineer is, or otherwise the specifically qualified person, such as a doctor, a nurse and a clinical inspection engineer or the expert engineer goes to a residence of the test subject to collect the biological sample from the test subject. In addition, an operation for preparing the sample for quantification from the collected biological sample has been performed by the specifically qualified person, such as a doctor, a nurse and a clinical inspection engineer or the expert engineer.

Since upon preparing the sample for quantification, it is required to quantify a specified volume thereof accurately, and accordingly this is rather troublesome, it has not been practiced that the test subject quantifies a specified volume of biological sample to prepare the sample for quantification or that the specifically qualified person or the expert engineer prepares the sample for quantification from the collected biological sample right on the spot of collection.

As a result of an improved performance of an automatic analyzer, a sample volume to be subjected to the inspection has been decreased, and accordingly such a large amount of biological sample as it has been is not now required to be collected. As the automatic analyzer using a method in which the element to be quantified is quantified by using a sample prepared by diluting a specified volume of biological sample by a specified volume of diluent solution is known Bio Majesty JCA-BA1650 (provided by JEOL).

However, in the normal blood collection system, since the supernatant blood plasma has to be sucked by a dropping pipet and transferred into a special container prepared for blood plasma analyses after the collected blood has been centrifugally separated, the operation for separating the blood into the blood cell and the blood plasma has taken rather long time, leading to higher cost, and further the operation for transferring the blood plasma into the special container has a potential risk of mix-up or the similar accidents.

Still further, due to the fact that the blood cell in the blood is hemolyzing as time goes by and the accuracy guarantee period of the blood left at ambient temperature is not more than one day, in the case where the test has been conducted after that period, there occurs some problems that affect test results or measured values to be no more available as a polestar for medical care and diagonosing, including that the measured values of electrolytic materials, such as sodium, kalium, chrome and the likes, might be adversely effected in their accuracy and the numeric values of enzyme system, such as GOT, GPT and the likes could not be measured.

Yet further, to separate the blood by a centrifugal separator and to conduct a test on predetermined items, the blood amount of about 5 to 10 ml is required for each collection. Accordingly, since it is difficult for a test subject in person to collect the blood, but a specifically qualified person, such as a doctor, has to collect the blood, the person of test subject is required to go to the hospital or the likes, or otherwise the qualified person has to go to the place of the person of test subject, thus requiring a long time and much labor for blood collection.

On the other hand, in the self-blood collection, since a series of steps is required comprising impregnating the blood into a filter paper, drying the filter paper, and then dissolving the filter paper into a solvent, the self-blood collection is usable to the test exclusively on such item that the test value could not be affected by going through those steps, but is not employable for the test on the other items.

In a manner of conventional clinical diagnosis, the specifically qualified person, such as a doctor, a nurse and a clinical inspection engineer or the expert engineer as well as the test subject have to bear heavy burden respectively, and a process from the collection of the biological sample to the practical inspection has been rather complicated. Accordingly, it has been desired to develop an inventive method of diagnosis in which the burden of the specifically qualified person, such as a doctor, a nurse and a clinical inspection engineer or the expert engineer as well as the test subject should be minimized, and to build up a simple clinical diagnosis system with said inventive method of diagnosis incorporated therein.

Accordingly, the present invention, in the light of the problems described above, provides an inventive instrument and method for separating blood, which accomplishes a reduction of cost in a blood test, a longer shelf life of the blood, and an improved test accuracy with a small amount of blood to be collected and a simplified operation.

Further, the present invention has been made to provide a method for preparing a sample for quantification from a biological sample, which is to be used for quantifying elements to be quantified in said biological sample; a method for quantifying the elements to be quantified in the biological sample; a container for preserving an unknown volume of biological sample containing elements to be quantified, which has been collected without quantifying a volume thereof, until it will be quantified; and a container used for preparing a sample for quantification from an unknown volume of biological sample containing elements to be quantified, which has been collected without quantifying a volume thereof.

SUMMERY OF THE INVENTION

The present invention is made in the light of the situations described above and has features below to solve the problems mentioned above. That is to say, a blood separating instrument according to the present invention comprises: a blood collection device for containing collected blood; a filtration device for separating blood cell and blood plasma in said collected blood; a blood cell collection device for containing separated blood cell; a blood plasma collection device for containing separated blood plasma; and a pressure applying device for applying pressure to the blood contained in said blood collection device; wherein said filtration device includes a capillary having one end in communication with a blood discharging section of said blood collection device and the other end in communication with a blood cell introducing section of said blood cell collection device, said capillary having a plurality of perforations formed through a wall thereof with a size to allow the blood plasma to pass therethrough but to prevent the blood cell from passing therethrough, so that when the blood in said blood collection device is introduced into said filtration device by a pressure applying motion caused by said pressure applying device, the blood plasma in said blood may move through said perforations of said filtration device to be separately contained in said blood plasma collection device.

In a preferred aspect of the present invention, a blood separating instrument comprises: a main container body having a blood collection container portion for containing collected blood, a blood plasma collection container attaching/detaching portion in communication with a blood discharging section of said blood collection container portion, and a blood cell collection container attaching/detaching portion whose blood cell introducing section is in communication with said blood plasma collection container attaching/detaching portion; a push-in cap having a push-in section which is adapted to be fittingly inserted into said blood collection container portion; a blood plasma collection container detachably connected with said blood plasma collection container attaching/detaching portion and containing a predetermined amount of blood plasma dilution; a blood cell collection container detachably connected with said blood cell collection container attaching/detaching portion and containing a predetermined amount of blood cell protective solvent; and an ultrafiltration element for separating the blood cell and the blood plasma in said blood; wherein said ultrafiltration element has a group of capillaries made of filter paper each having one end in communication with said blood discharging section of said blood collection container portion and the other end in communication with said blood cell introducing section of said blood cell collection container, said capillary having a plurality of perforations formed through a wall thereof with a size to allow the blood plasma to pass therethrough but to prevent the blood cell from passing therethrough, so that when the blood in said blood collection container portion is introduced into said ultrafiltration element by a pushing-in motion of said push-in cap, the blood plasma in said blood may move through said perforations of said ultrafiltration element to be separately contained in said blood plasma collection container.

Further, in a preferred aspect of the present invention, an inner diameter of the perforation of said capillary is within a range of 0.4 to 0.6 μm, said blood collection container portion contains spherical solvent enclosed by a sheet wall arranged in a bottom portion thereof, said push-in section of said push-in cap has an end portion capable of collapsing said sheet wall, and an outer diameter of each element of said spherical solvent is greater than the inner diameter of the perforation of said capillary.

Still preferably, a volume of said blood collection container portion is within a range of 80 to 120μ liter, and said instrument of the present invention further comprises a piston which divides the inside of said blood cell collection container into an air layer region and a blood cell protective solvent containing region and is capable of slidably moving therein, wherein a pressure in said air layer region is set to be within a range of 1.0 to 1.5 atm., and said blood plasma dilution is mixed with a predetermined amount of pigment.

A blood separating method according to the present invention comprises the steps of: collecting blood into a blood collection device; applying a pressure to said blood by a pressure applying device to introduce said blood into a filtration device whose one end communicates with a blood discharging section of said blood collection device; containing blood plasma in said blood into a blood plasma collection device through perforations formed through a wall of said filtration device; and making blood cell in said blood flow through said filtration device to be contained in a blood cell collection device through a blood cell introducing section of said blood cell collection device, with which the other end of said filtration device communicates.

In a preferred aspect of the present invention, a blood separating method comprises the steps of; collecting blood into a blood collection container portion of a main container body; fittingly inserting and pushing-in a push-in cap into said blood collection container portion immediately after said collecting step to introduce said blood into a capillary of an unltrafiltration element whose one end communicates with a blood discharging section of said blood collection container portion; dissolving blood plasma in said blood through perforations formed through a wall of said capillary into blood plasma dilution contained in a blood plasma collection container connected air-tightly with said main container body,; and making blood cell in said blood flow through said ultrafiltration element to be mixed into blood cell protective solvent contained in a blood cell collection container connected air-tightly with said main container body through a blood cell introducing section of said blood cell collection container with which the other end of said ultrafiltration element communicates.

Further, in a preferred aspect of the present invention, said push-in section of said push-in cap is pushed-in to reach to the lowest level to collapse a sheet wall arranged in a bottom portion of said blood collection container for enclosing the spherical solvent and to fill up each of said capillaries with said spherical solvent to be coagulated therein, and further said blood is collected in an amount of 80 to 120μ liter.

According to the present invention described above, said blood flows from said blood collection device into the capillary of said filtration device, wherein the blood plasma of said blood passes through the perforations of said capillary to be contained in said blood plasma collection device, while the blood cell of said blood flows through said capillary to be contained in said blood cell collection device.

Further, the present invention provides inventive methods and containers as described below in (14) to (41):

(14) A preparing method for preparing a sample for quantification from a biological sample, which is to be used for quantifying elements to be quantified in said biological sample, said method characterized in comprising a step of mixing an unknown volume of biological sample collected without quantifying a volume thereof with a specified volume of aqueous solution;

(15) A preparing method in accordance with (14), in which said specified volume of aqueous solution contains a specified amount of indicating material;

(16) A preparing method in accordance with (14), characterized in further comprising a step of adding a specified volume of aqueous solution containing a specified amount of indicating material;

(17) A preparing method in accordance with (14), in which said indicating material is a pigment or a chromogen;

(18) A preparing method in accordance with (17), in which said chromogen is an oxidative coloring type chromogen;

(19) A preparing method in accordance with (14), in which said biological sample is either one of a whole blood, a blood plasma or a blood serum;

(20) A preparing method in accordance with (14), in which said aqueous solution is a buffer solution;

(21) A preparing method in accordance with (14), in which said elements to be quantified are elements in the blood serum;

(22) A quantifying method for quantifying elements to be quantified in a biological sample, said method characterized in using a sample for quantification prepared by a preparing method comprising a step of mixing an unknown volume of biological sample collected without quantifying a volume thereof with a specified volume of aqueous solution containing a specified amount of indicating material;

(23) A quantifying method in accordance with (22), in which said unknown volume of biological sample collected without quantifying a volume thereof is mixed with a specified volume of aqueous solution;

(24) A quantifying method in accordance with (22), said method characterized in further comprising the steps of:
determining a dilution ratio of said biological sample in said sample for quantification; and
quantifying a concentration of the elements to be quantified in said sample for quantification;

(25) A quantifying method in accordance with (22), in which said indicating material is a pigment or a chromogen;

(26) A quantifying method in accordance with (25), in which said chromogen is an oxidative coloring type chromogen;

(27) A quantifying method in accordance with (22), in which said biological sample is either one of a whole blood, a blood plasma or a blood serum;

(28) A quantifying method in accordance with (22), in which said aqueous solution is a buffer solution;

(29) A quantifying method in accordance with (22), in which said elements to be quantified are elements in the blood serum;

(30) A container for preserving biological sample used for preserving an unknown volume of biological sample containing elements to be quantified, which has been collected without quantifying a volume thereof, until it will be quantified, said container being filled with a specified volume of aqueous solution, and said container having a closable opening/closing device for adding said biological sample;

(31) A container for preparing a sample for quantification used for preparing a sample for quantification from an unknown volume of biological sample containing elements to be quantified, which has been collected without quantifying a volume thereof, said container being filled with a specified volume of aqueous solution, and said container having a closable opening/closing device for adding said biological sample;

(32) A container in accordance with (30), in which said specified volume of aqueous solution is a solution containing a specified amount of indicating material;

(33) A container in accordance with (32), in which said indicating material is a pigment or a chromogen;

(34) A container in accordance with (33), in which said chromogen is an oxidative coloring type chromogen;

(35) A container for collecting a biological sample in accordance with (30), in which said biological sample is either one of a whole blood, a blood plasma or a blood serum;

(36) A container for collecting a biological sample in accordance with (30), in which said elements to be quantified are elements in the blood serum;

(37) A quantifying method for quantifying elements to be quantified in a biological sample, said method comprising the steps of:
1) preparing a sample for quantification composed of an unknown volume of biological sample containing elements to be quantified, which has been collected without quantifying a volume thereof, and a specified volume of aqueous solution containing a specified amount of indicating material;
2) determining a dilution ratio (a) of said biological sample from a concentration ($C_1$) of the indicating material in said specified volume of aqueous solution containing said specified amount of indicating material and a concentration ($C_2$) of the indicating material in said sample for quantification;
3) determining a concentration (Y) of the elements to be quantified in said sample for quantification; and
4) determining the elements to be quantified in the biological sample based on the dilution ratio (a) of the biological sample determined in the step 2) and said concentration (Y) of the elements to be quantified in the sample for quantification determined in the step 3);

(38) A quantifying method in accordance with (37), in which said aqueous solution is a buffer solution;

(39) A method in accordance with (37), in which said indicating material is a pigment or a chromogen;

(40) A method in accordance with (39), in which said chromogen is an oxidative coloring type chromogen;

(41) A method in accordance with (39), in which an absorptivity ($E_1$) of said specified volume of aqueous solution containing said specified amount of indicating material and an absorptivity ($E_2$) of said sample for quantification are used in substitution for $C_1$ and $C_2$ respectively.

DESCRIPTION OF THE PREFERRED EMBODIMENTS

A preferred embodiment of the present invention will now be described with reference to the attached drawings.

Figure 1:
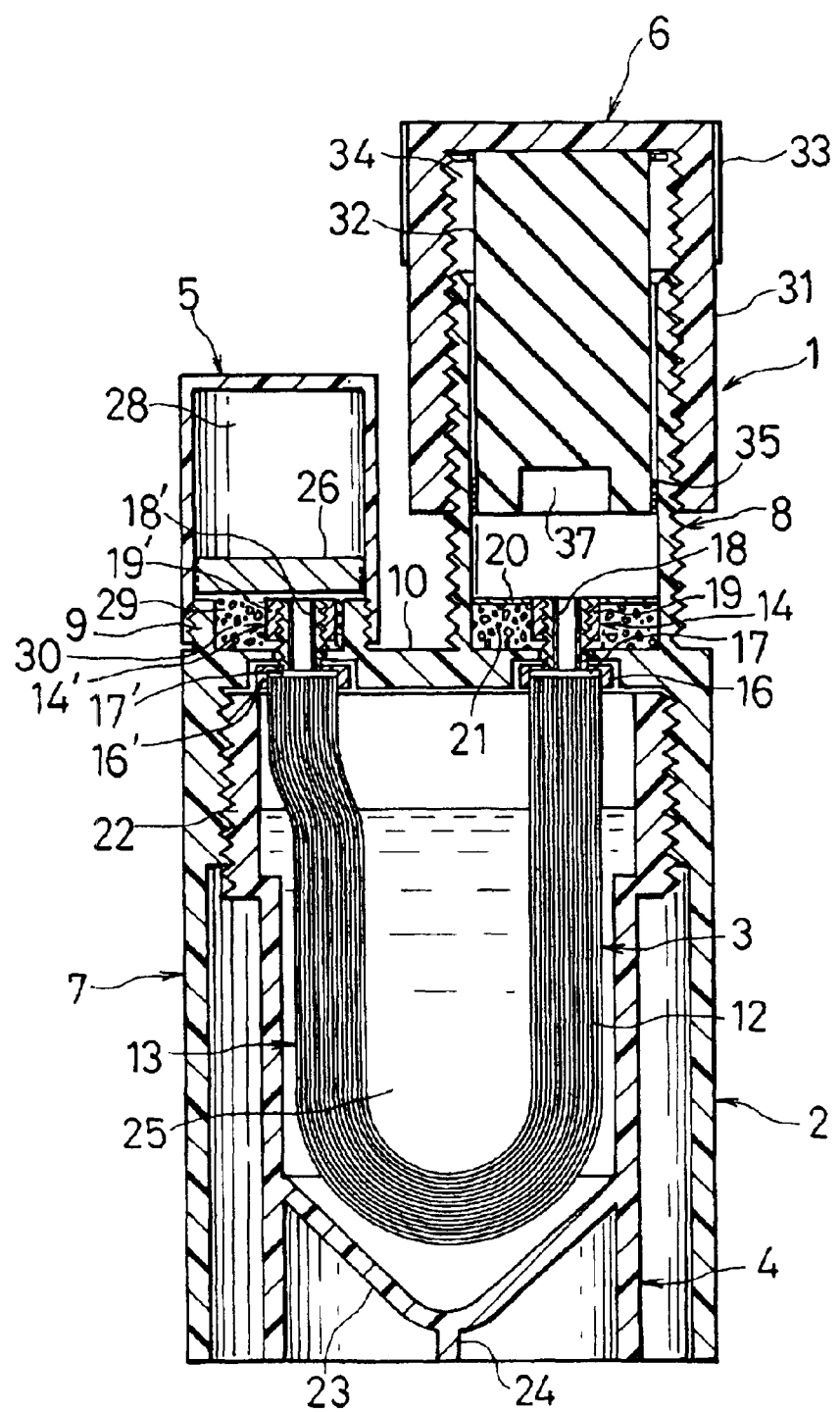
FIG. 1 is a cross sectional view of an embodiment of the present invention.

FIG. 1 shows a blood separating instrument 1 according to the present invention, which comprises: a main container body 2; an ultrafiltration element 3 connected with said main container body 2; a blood plasma collection container 4 and a blood cell collection container 5, both of which are respectively detachably connected with said main container body 2; and a push-in cap 6 adapted to be fittingly inserted into said main container body 2; wherein said main container body 2, said blood plasma collection container 4 and said blood cell collection container 5 are typically made of synthetic resin.

Figure 2:
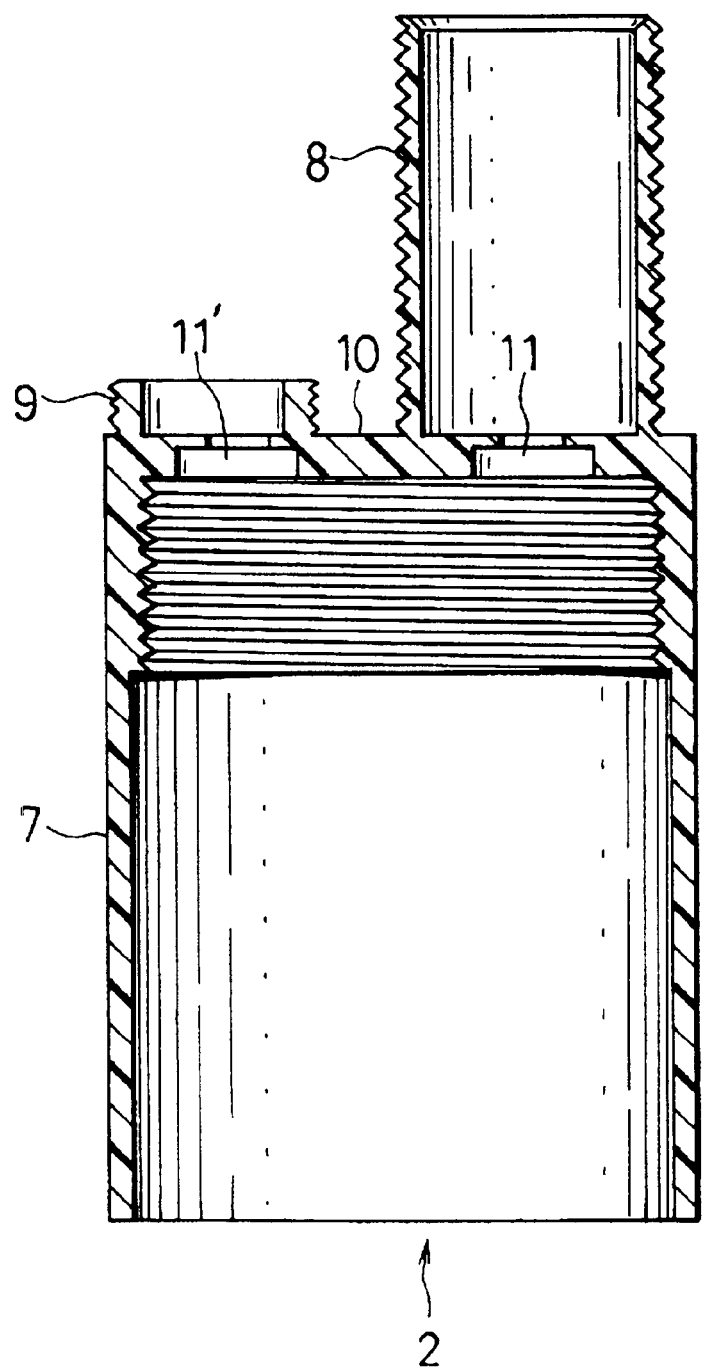
FIG. 2 is a cross sectional view of a main container body according to the present invention.
Figure 3:
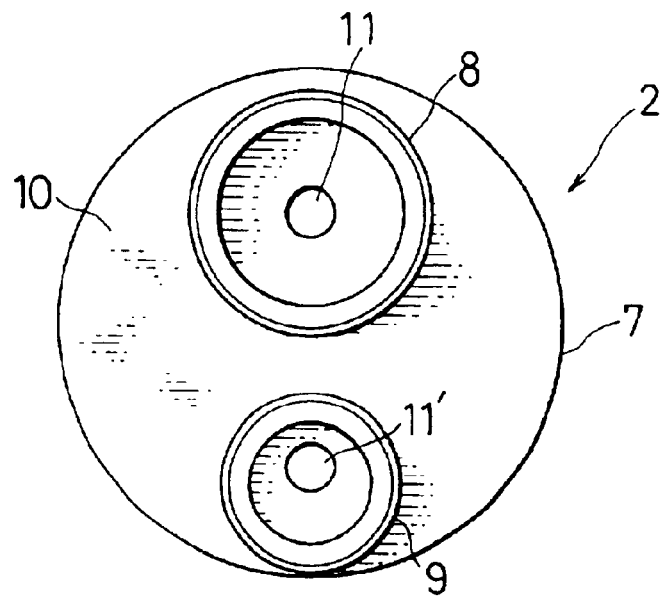
FIG. 3 is a top view of the main container body according to the present invention.
Figure 4:
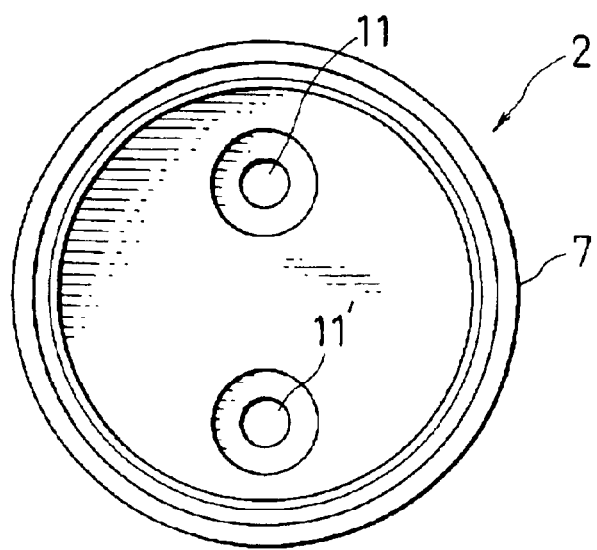
FIG. 4 is a bottom view of the main container body according to the present invention.

Referring to FIGS. 2 to 4, said main container body 2 is formed into a cylindrical shape having a ceiling and comprises a blood plasma collection container attaching/detaching portion 7 having an inner diameter of, for example, about 1.5 cm, and a blood collection container portion 8 and a blood cell collection container attaching/detaching portion 9, each being formed into a cylindrical shape on said blood plasma collection container attaching/detaching portion 7 respectively, wherein said blood collection container portion 8 has a bore diameter and a height both being greater than those of said blood cell collection container attaching/detaching portion 9. Preferably, said blood collection container portion 8 has a volume within a range of 80 to 120µ liter (equivalent to 4 or 5 drops of blood), and more preferably a volume of 100µ liter, that is, for example, when the bore diameter is 8 mm, the depth is about 2 mm. A blood discharging channel 11 and a blood cell introducing channel 11' are formed through a top plate 10 of said blood plasma collection container attaching/detaching portion 7, so that said blood collection container portion 8 communicates with said blood plasma collection container attaching/detaching portion 7 through said blood discharging channel 11, and said blood cell collection container attaching/detaching portion 9 communicates with said blood plasma collection container attaching/detaching portion 7 through said blood cell introducing channel 11'. Said blood plasma collection container attaching/detaching portion 7 is threaded in the upper inner side thereof, while said blood collection container portion 8 and said blood cell collection container attaching/detaching portion 9 are respectively threaded in the outer sides thereof.

Figure 5:
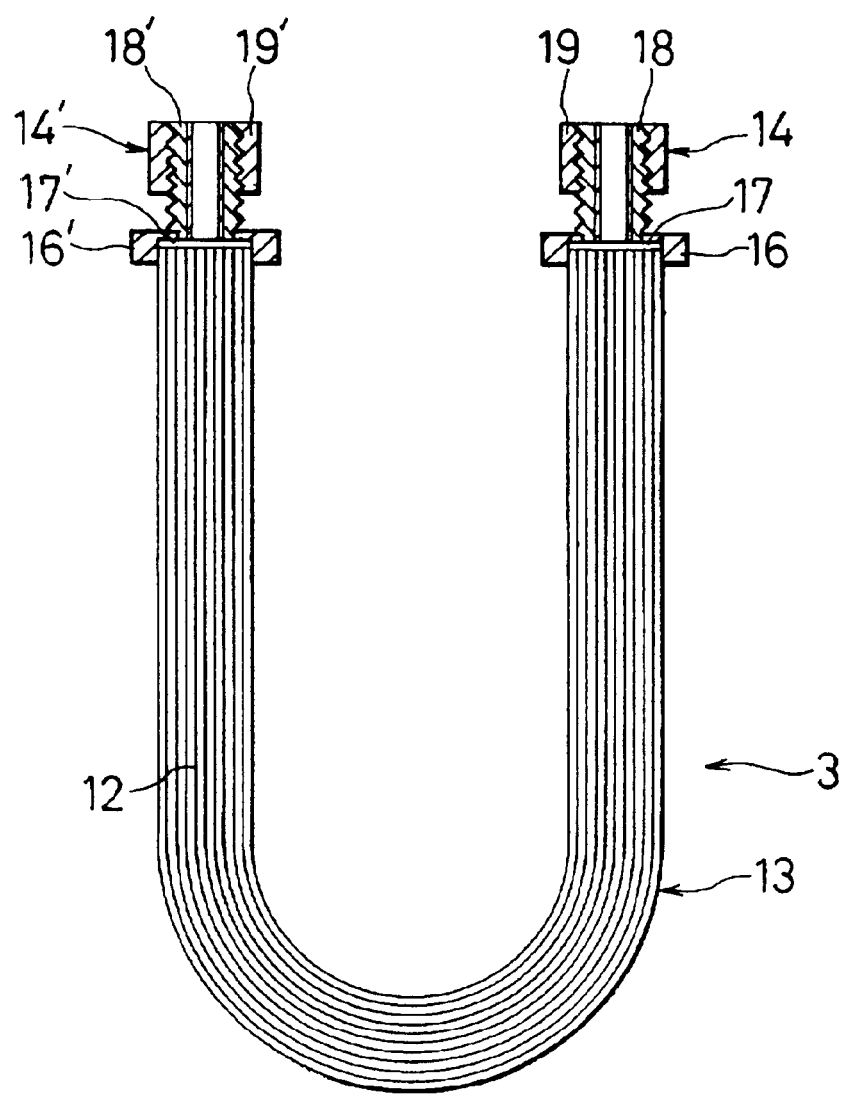
FIG. 5 is a schematic view of an ultrafiltration element of the present invention.
Figure 6:
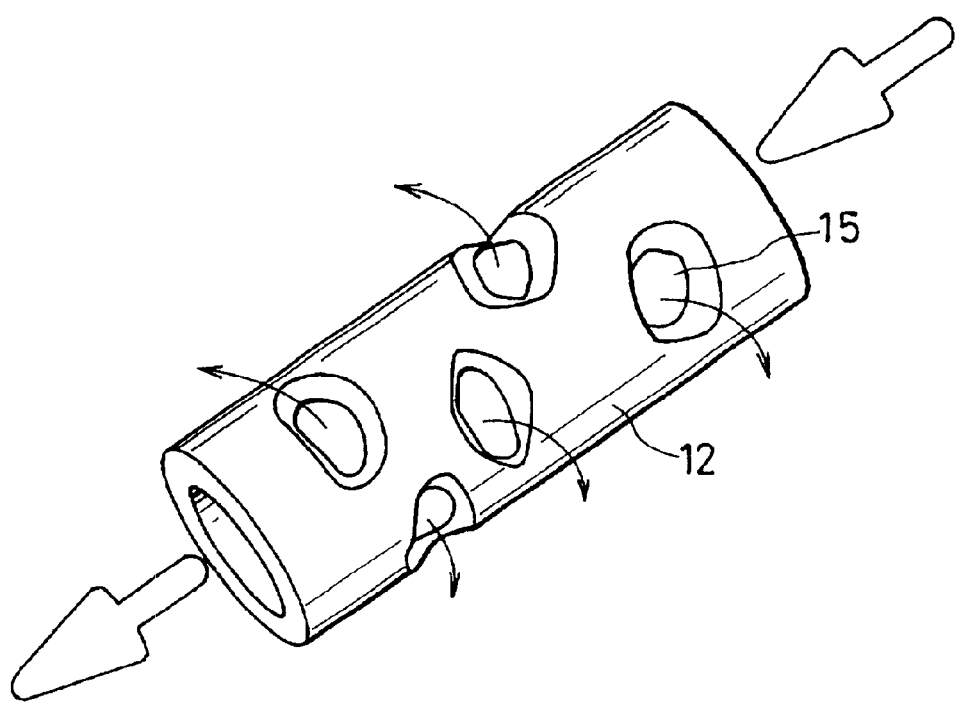
FIG. 6 is a partial perspective view of a capillary according to the present invention.
Figure 7:
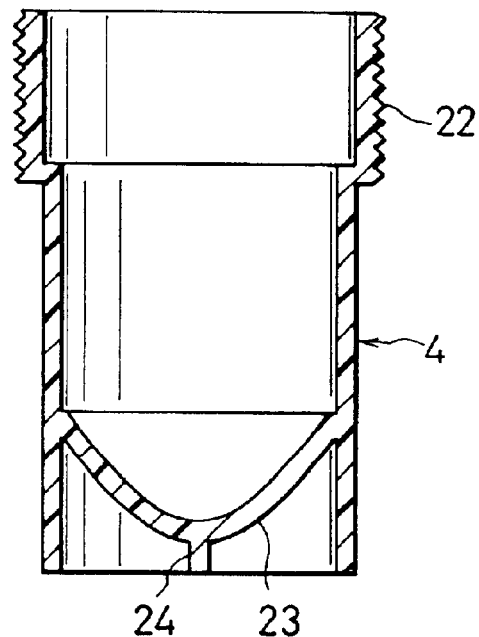
FIG. 7 is a cross sectional view of a blood plasma collection container according to the present invention.
Figure 8:
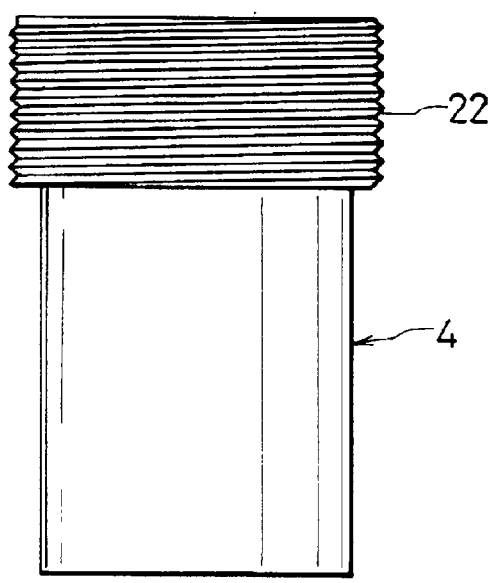
FIG. 8 is a side elevational view of the blood plasma collection container according to the present invention.
Figure 9:
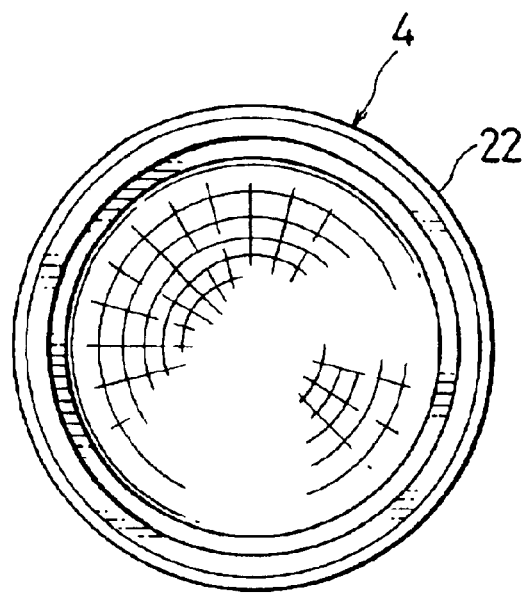
FIG. 9 is a top view of the blood plasma collection container according to the present invention.
Figure 10:
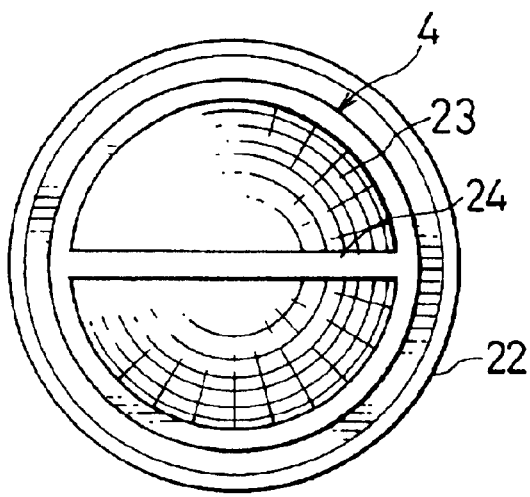
FIG. 10 is a bottom view of the blood plasma collection container according to the present invention.
Figure 11:
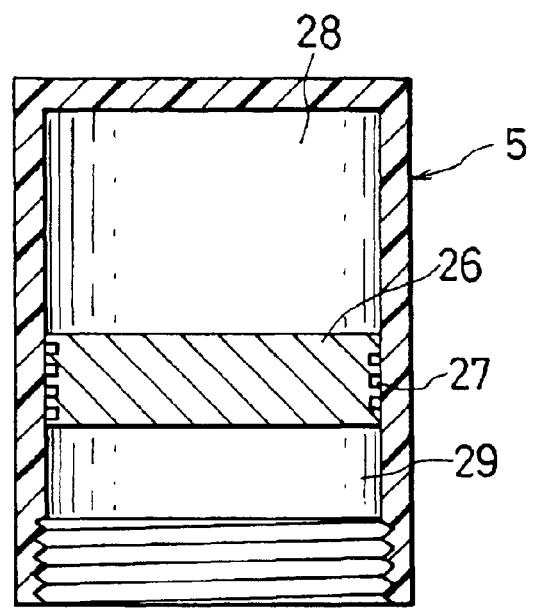
FIG. 11 is a cross sectional view of a blood cell collection container according to the present invention.
Figure 12:
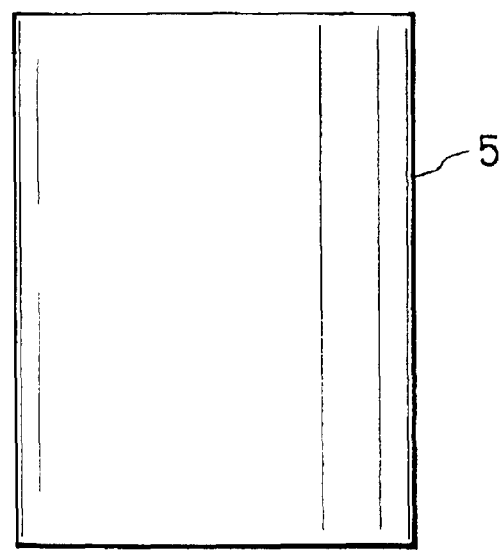
FIG. 12 is a side elevational view of the blood cell collection container according to the present invention.
Figure 13:
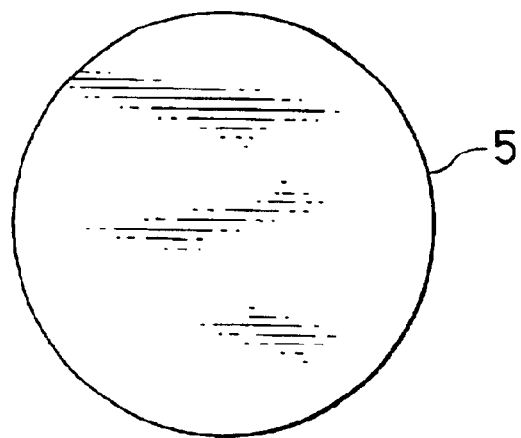
FIG. 13 is a top view of the blood cell collection container according to the present invention.
Figure 14:
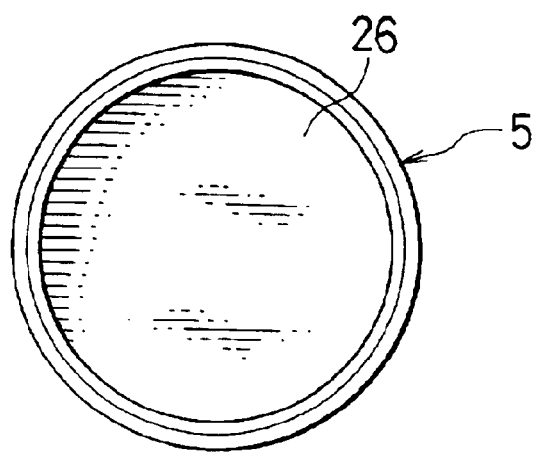
FIG. 14 is a bottom view of the blood cell collection container according to the present invention.
Figure 15:
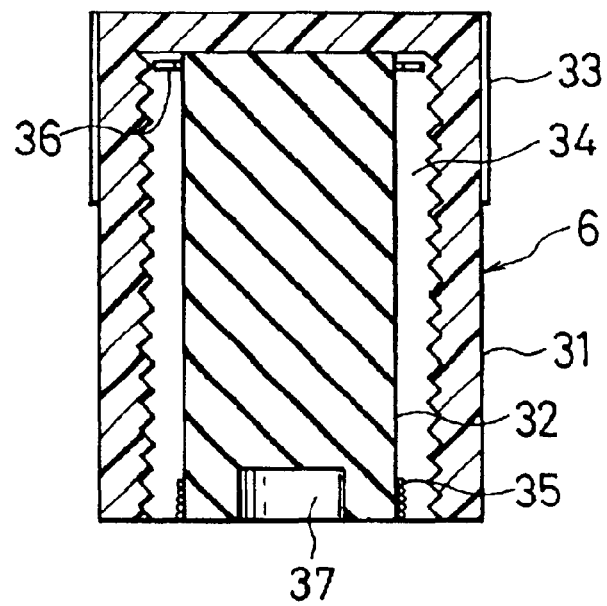
FIG. 15 is a cross sectional view of a push-in cap according to the present invention.
Figure 16:
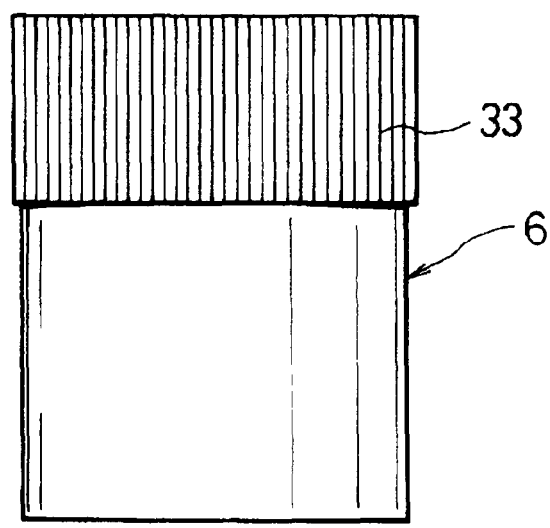
FIG. 16 is a side elevational view of the push-in cap according to the present invention.
Figure 17:
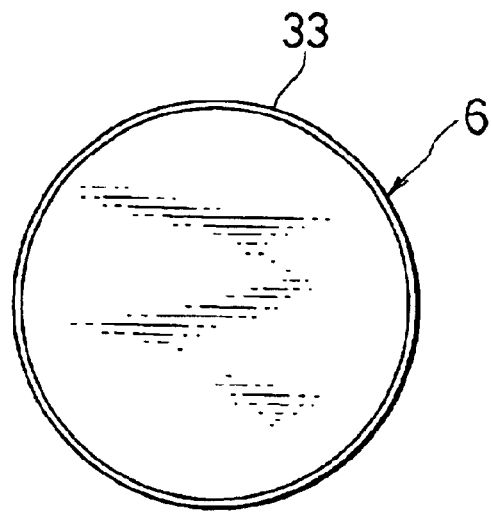
FIG. 17 is a top view of the push-in cap according to the present invention.
Figure 18:
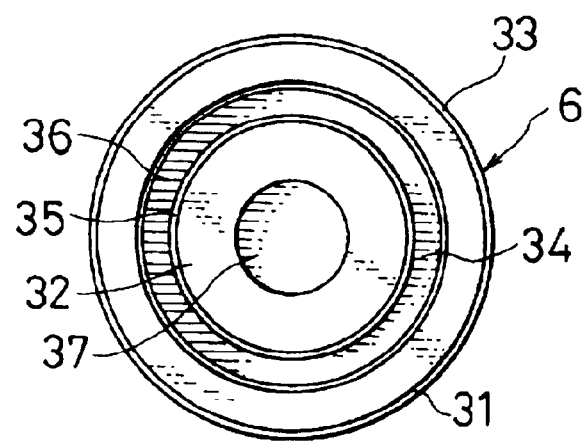
FIG. 18 is a bottom view of the push-in cap according to the present invention.

As shown in FIGS. 1, 5 and 6, said ultrafiltration element 3 has a filtering section 13 comprising a plurality of capillaries 12, for example, 100 strings of capillaries made of filter paper (e.g. each of capillaries having the bore diameter of 2 mm and the total length of 3 cm), and a connecting section 14 and 14' respectively arranged in either end portions of said filtering section 13, in which each of said capillaries 12 has a plurality of perforations 15 formed through a wall thereof, said perforation preferably having an inner diameter within a range of 0.4 to 0.6 µm and more preferably an inner diameter of 0.5 µm. Each of said connection sections 14 and 14' has a flat pedestal 16 or 16' for respectively binding said capillaries 12, and each of said pedestals 16 and 16' is adapted to form a confluent section 17 or 17' of flat space inside thereof as respectively binding said capillaries 12. Further, conduits 18 and 18' are respectively fixedly attached onto the upper central portions of ceilings of said pedestals 16 and 16' to communicate with said confluent sections 17 and 17', said conduits 18 and 18' being threaded on the outer surfaces respectively. Said conduits 18 and 18' are respectively arranged so as to pass through said blood discharging channel 11 and said blood cell introducing channel 11' from the blood plasma collection container attaching/detaching portion 7 side respectively, wherein said conduit 18 is to be engaged with a nut 19 screwed from said blood collection container portion 8 side, while said conduit 18' is to be engaged with a nut 19' screwed from said blood cell collection container attaching/detaching portion 9 side, so that said nuts 19 and 19' and said pedestals 16 and 16' cooperate to clamp the top plate 10 of said blood plasma collection container attaching/ detaching portion 7. Further, said blood collection container portion 8 has a sheet wall 20 made of material capable of being collapsed, such as synthetic rubber, horizontally extended across the bottom portion thereof, and said conduit 18 is arranged so as to air-tightly penetrate said sheet wall 20, wherein under said sheet wall 20 is contained a predetermined amount of artificial spherical solvent 21 composed of elements each having an outer diameter larger than the inner diameter of said perforation 15 of said capillary 12, preferably about 0.2 $\mu$m greater than the inner diameter of said perforation 15.

Referring to FIG. 1 and FIGS. 7 to 10, said blood plasma collection container 4 is formed into an approximately cylindrical shape having an expanded diameter section 22 arranged in the upper portion thereof and a bottom section 23 arranged in the lower portion thereof, preferably such a shape that allows the container 4 to be directly set in a blood plasma analyzer (not shown). Said expanded diameter section 22 is threaded on the outer surface thereof so that the expanded diameter section 22 may be screwed into and engaged with said blood plasma collection container attaching/detaching portion 7. Said bottom section 23 is formed into cone shape having a pinch section 24 protruding on the bottom surface along a radial direction so that said blood plasma collection container 4 could be attached to/detached from said blood plasma collection container attaching/detaching portion 7 by horizontally rotating said pinch section 24. Still further, said blood plasma collection container 4 receives blood plasma dilution 25 contained therein and in addition, pigment of malachite green or the like mixed in said blood plasma dilution 25.

Referring to FIG. 1 and FIGS. 11 to 14, said blood cell collection container 5 is formed into a cylindrical shape having ceiling, and is threaded on an inner lower portion thereof so that the container 5 is allowed to be attached to/detached from said blood cell collection container attaching/detaching portion 9. Further, a piston 26 formed into flat column or thick disk is arranged in said blood cell collection container 5 so as to be capable of sliding up and down therein. Preferably, a plurality of small grooves is carved on a peripheral wall of said piston 26 along a circular direction thereof, so that air tightness between the inner surface of said blood cell collection container 5 and said piston 26 may be retained while allowing said piston 26 to slide along said inner surface. The inside of said blood cell collection container 5 is divided by said piston 26 into two chambers, the chamber above said piston 26 defining an air layer region 28 while the other chamber beneath said piston 26 defining a blood cell protective solvent containing region 29. In order to prevent blood cell clotting and hemolysis, said blood cell protective solvent containing region 29 receives a blood cell protective solvent 30, for example, an anticoagulant such as EDTA or citric acid, contained therein, with the volume of about ⅕ of blood cell volume to be collected. Further, a pressure inside said air layer region 28 is kept in a level higher than the outside pressure, preferably 0.2 to 1.0 higher than the outside pressure so that said piston 26 may be in contact with said connecting section 14', in the initial state, preventing the backflow of said blood cell protective solvent 30 into said filtering section 13.

Referring to FIG. 1 and FIGS. 15 to 18, said push-in cap 6 comprises an outer peripheral section 31 of cylindrical shape having a ceiling and made of synthetic resin, and a push-in section 32 of column shape made of synthetic rubber and fixedly connected to an inner surface of the top plate of said outer peripheral section 31 to be concentric therewith, wherein said outer peripheral section 31 is provided with a non-slip section 33 arranged on the upper outer surface thereof and is threaded on an inner peripheral surface thereof. Between said outer peripheral section 31 and said push-in section 32 is formed a space 34 of cylindrical shape, so that said outer peripheral section 31 could be screwed over said blood collection container portion 8 and thereby said push-in section 32 could be guided to be fittingly inserted into said blood collection container portion 8. On a lower portion of the peripheral wall of said push-in section 32 is arranged a sealing member, for example, a plurality of rings 35 made of resilient material, for retaining the airtightness between said push-in section 32 and said blood collection container portion 8 while the former being fittingly inserted into the latter. Further, a packing 36 in the form of annular sheet plate is fixedly attached to a top portion of the peripheral wall of said push-in section 32, so that the air-tightness between said blood collection container portion 8 and said push-in cap 6 is retained by pressing the top end of said blood collection container portion 8 against said packing 36. Still further, a concave portion 37 is concentrically formed on the lower end of said push-in section 32, so that said concave portion 37 may be fittingly engaged with said nut 19.

A blood separating method according to the present invention will now be described with reference to the attached drawings.

Figure 19:
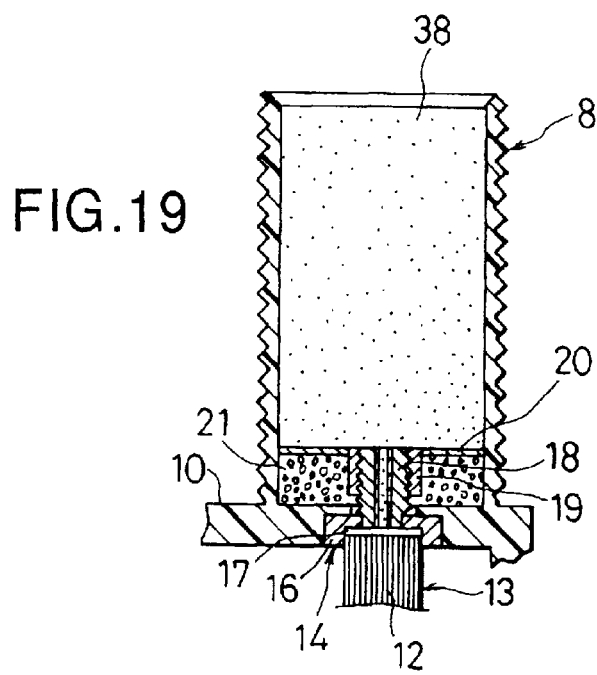
FIG. 19 is a cross sectional view, illustrating the blood having been collected in the blood collection container portion, according to the present invention.
Figure 20:
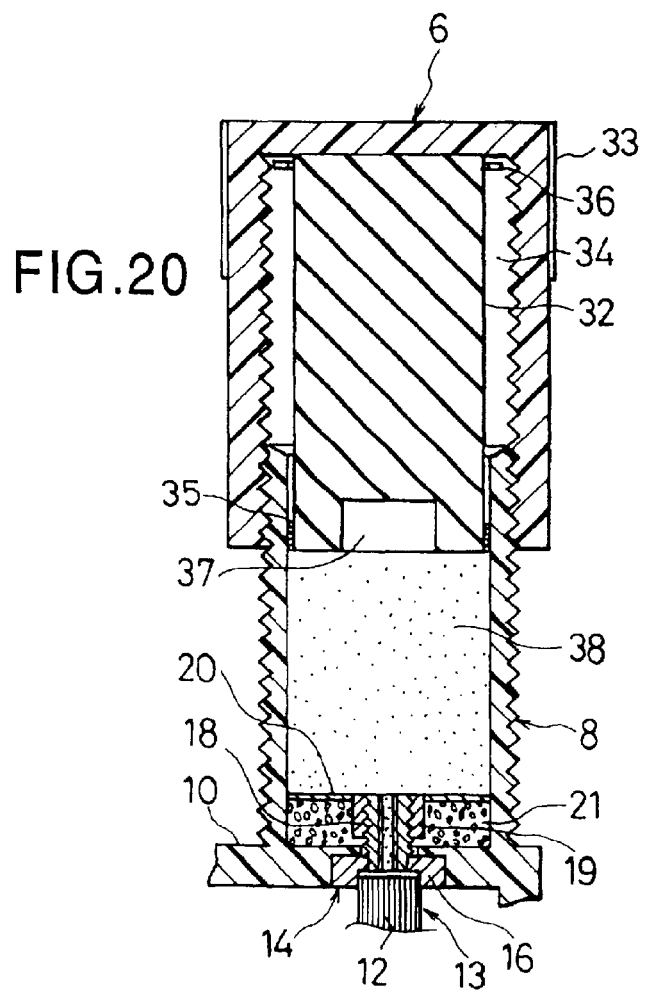
FIG. 20 is a cross sectional view, illustrating a push-in section of the push-in cap being pushed-in against the blood collection container portion, according to the present invention.

A person of test subject pricks a finger of his or her hand with a blood collecting needle to collect preferably 80 to 120$\mu$ liter (4 or 5 drops), more preferably 100$\mu$ liter of blood 38 into said blood collection container portion 8 as shown in FIG. 19. The person grasps said non-slip section 33, and fittingly inserts said push-in section 32 of said push-in cap 6 into said blood collection container portion 8 as shown in FIG. 20. The air tightness between said push-in section 32 and said blood collection container portion 8 is retained by said ring 35, said blood 38 is pressed by said push-in section 32 to flow through said conduit 18 into said respective capillaries 12 of said ultrafiltration element 3.

Since the blood plasma 39 in said blood 38 has an outer diameter smaller than the inner diameter of said perforation 15 of said capillary 12, therefore the blood plasma 39 goes through the perforation 15 to be dissolved into said blood plasma dilution 25 contained in said blood plasma collection container 4. With the help of the pigment mixed in the blood plasma dilution 25, a dilution ratio (dissolution ratio) of the solution could be accurately calculated by measuring a amount of the pigment per unit volume thus to keep the higher level of inspection accuracy of the blood plasma.

Figure 24:
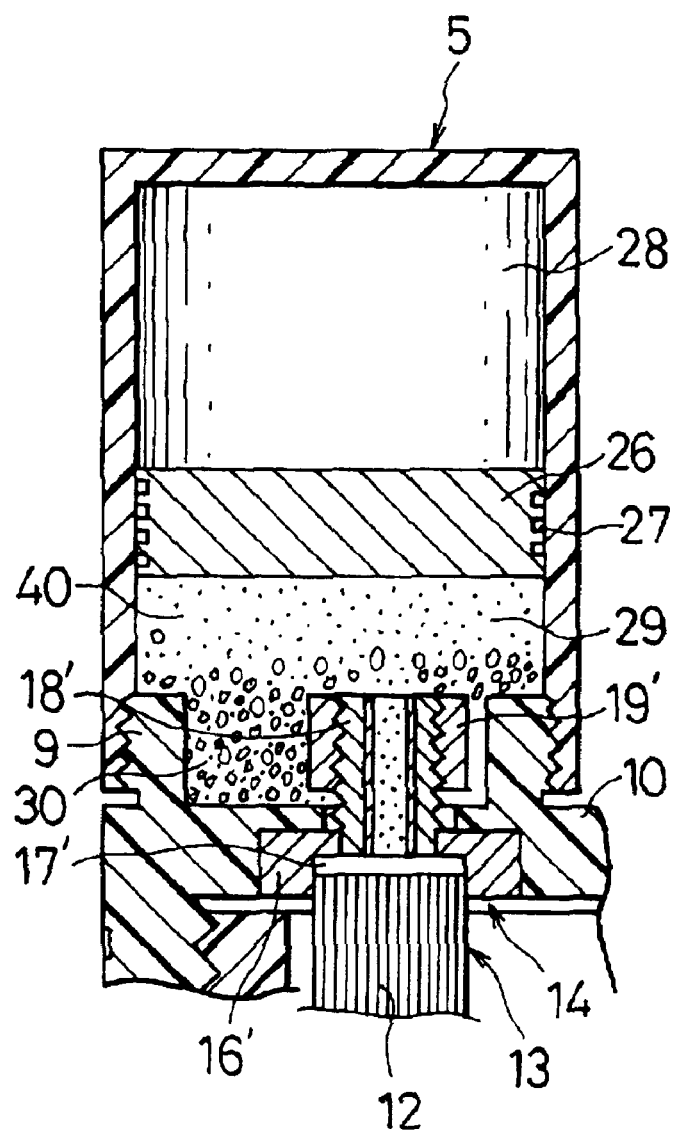
FIG. 24 is a cross sectional view, illustrating the blood cell starting to flow into the blood cell collection container, according to the present invention.
Figure 25:
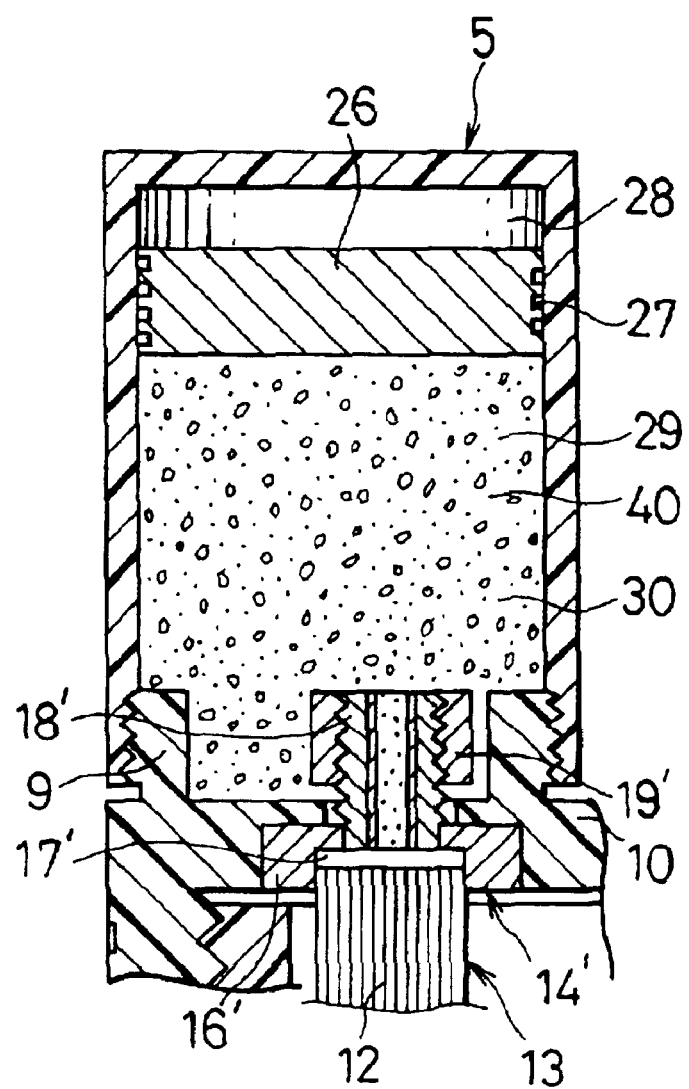
FIG. 25 is a cross sectional view, illustrating a piston being raised up temporarily, according to the present invention.
Figure 26:
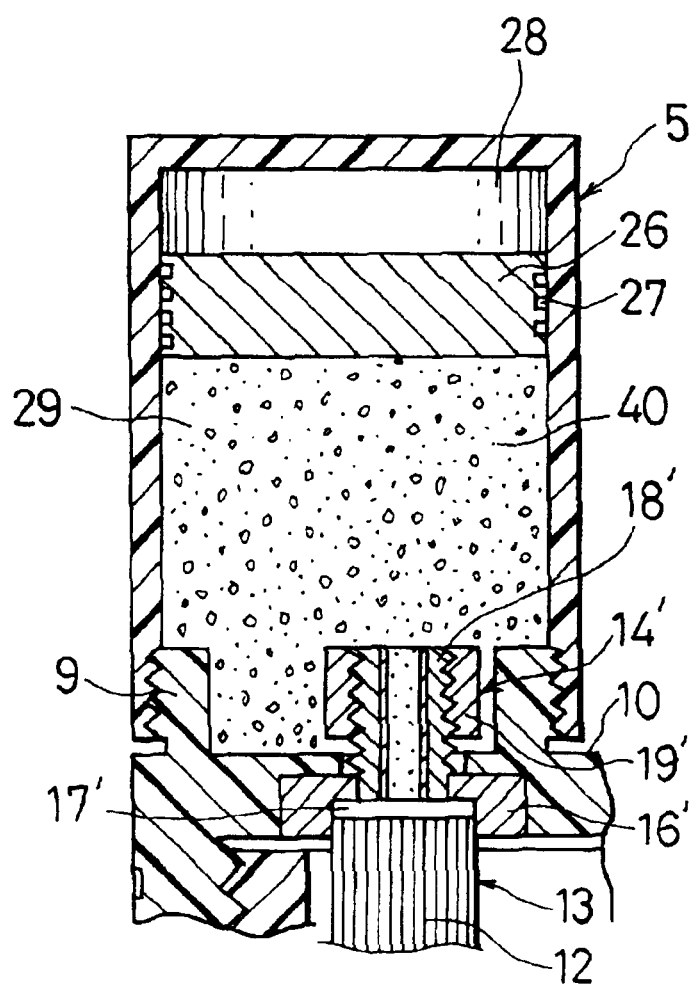
FIG. 26 is a cross sectional view, illustrating the inflow of the blood cell into the blood cell collection container having been completed, according to the present invention.

Further, since the blood cell 40 in said blood 38 has an outer diameter greater than the inner diameter of said perforation 15, the blood cell 40 flows through said respective capillaries 12 and said conduit 18' to raise the piston 26 as shown in FIG. 24, and to be finally mixed into said blood cell protective solvent 30 in said blood cell collection container 5. Since said grooves 27 are arranged on the peripheral wall of said piston 26, said piston 26 slidably moves upward while retaining the air-tightness between the inner peripheral surface of said blood cell collection container 5 and the piston 26. At that time, since it takes a certain period of time for said blood plasma 39 to pass through said perforation 15, said piston 26 is raised up temporarily as shown in FIG. 25 when said push-in section 32 is inserted at a burst, but since the pressure in said air region 28 is increased as the piston 29 is raised up, the increased pressure is then applied to said piston 26 to be slid down and to press said blood cell protective solvent 30 including said blood cell 40 mixed therein, thus accelerating said blood plasma 39 to pass through said perforation 15.

Figure 21:
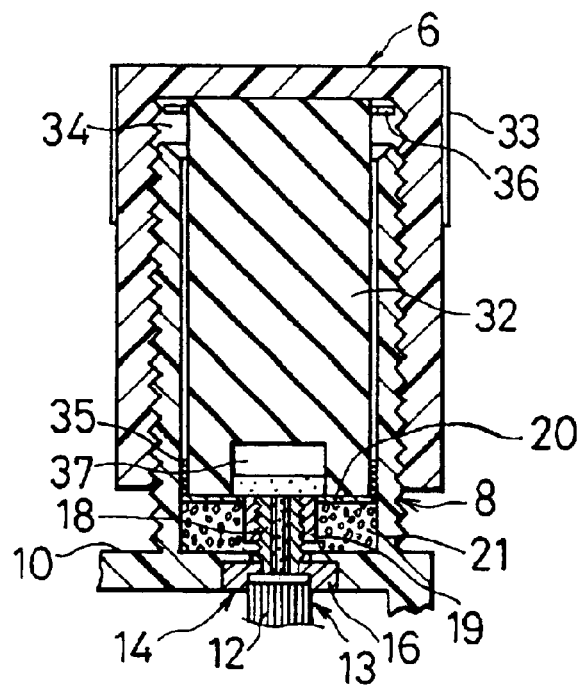
FIG. 21 is a cross sectional view, illustrating a sheet wall arranged in a bottom portion of the blood collection container portion being collapsed and a spherical solvent being discharged therefrom, according to the present invention.
Figure 22:
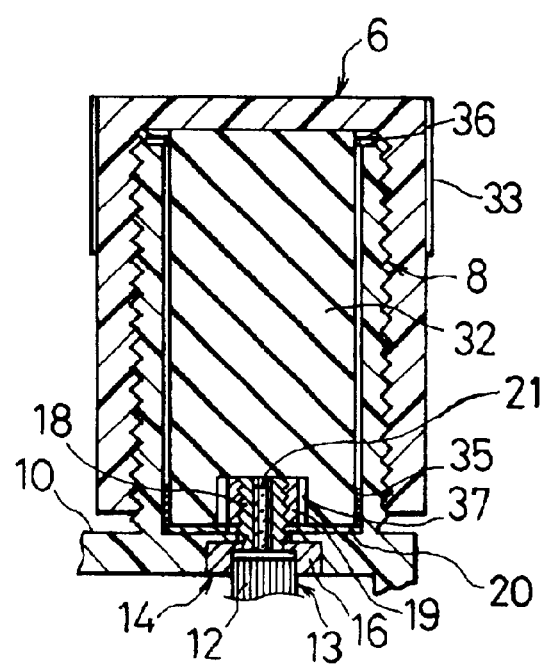
FIG. 22 is a cross sectional view, illustrating the push-in cap having been pushed-in to the lowest level, according to the present invention.
Figure 23:
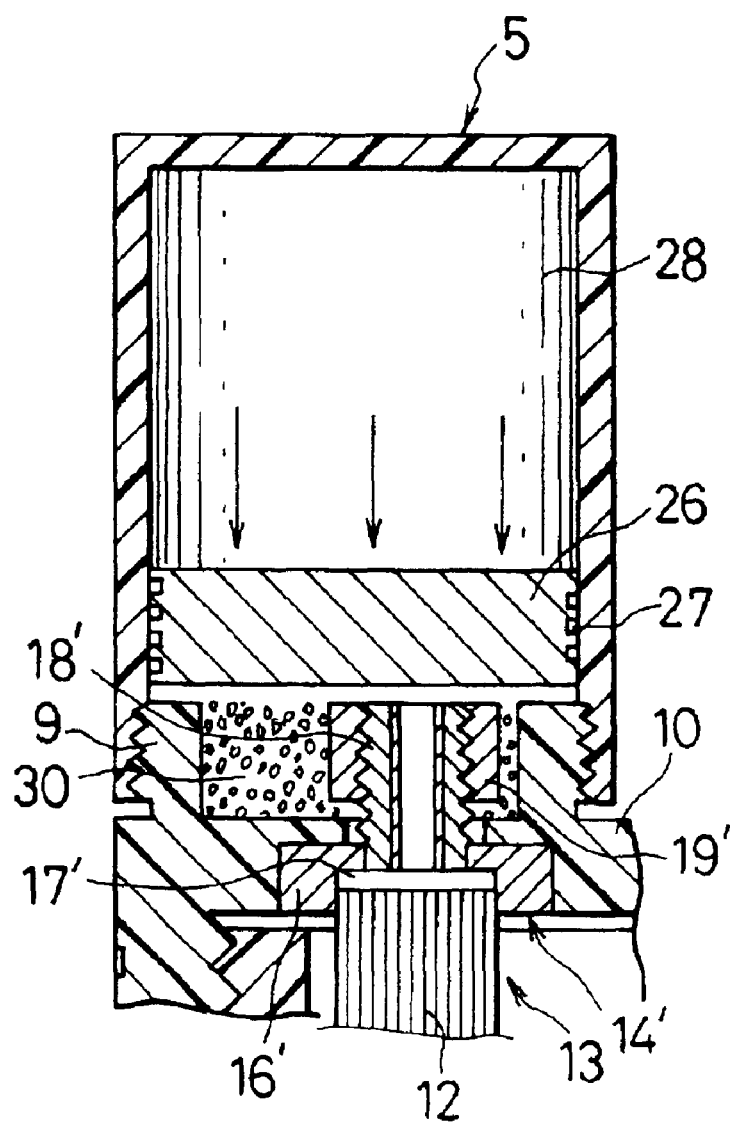
FIG. 23 is a cross sectional view, illustrating the blood cell collection container in its initial state, according to the present invention.

When said blood 38 in said blood collection container portion 8 has been completely discharged from said blood collection container portion 8, the lower end of said push-in section 32 collapses said sheet wall 20, and said spherical solvent 21 flows into said concave portion 37 of said push-in section 32 and pass though said conduit 18 into said respective capillaries 12, as shown in FIGS. 21 and 22. When the push-in section 32 of said push-in cap 6 has reached to the lowest level, all of said spherical solvent 21 has flown out of said blood collection container portion 8 to fill up said respective capillaries 12 to be coagulated therein.

Accordingly, after that, said blood plasma dilution 25 including said blood plasma 39 dissolved therein is prevented from backflowing from said blood plasma collection container 4 to said respective capillaries 12, and said blood cell protective solvent 30 including said blood cell 40 mixed therein is also prevented from backflowing from said blood cell collection container 5 to said respective capillaries 12. Further, when said push-in section 32 has been pushed down and has reached to the lowest level, the upper end of said blood collection container portion 8 presses said packing 36, so that the air-tightness between said push-in cap 6 and said blood collection container portion 8 could be doubly secured by said packing 36 in addition to the effect of said ring 35.

Subsequently, said blood separating instrument 1, having said blood 38 as separated into said blood plasma 39 and said blood cell 40, is carried to a test station for the test on determined items to be conducted.

In this case, since the blood has been separated into the blood plasma and the blood cell right on the spot immediately after the blood collection and then the blood is carried to the test station with the blood cell included in the blood cell protective solvent, therefore hemolysis, blood clotting and the likes in transit could be prevented. Accordingly, the shelf life of the blood could be improved, thus to enhance the test accuracy. Further, since the collected blood is conservable for about one week at ambient temperature, any arrangement, such as quick transportation or geographical consideration of a collection spot and a test station, is not necessary, thus to improve a degree of flexibility in operation. Still further, the blood separation could be done with only a few drops of collected blood because no centrifugal separator is used, and thus the self-blood collection is usable for the test on the items equivalent to those tested by employing a conventional normal blood collection.

It should be appreciated that, although in the embodiment described above, said blood plasma collection container 4, said blood cell collection container 5, and said push-in cap 6 are threaded respectively to be engaged with said main container body 2, any alternative connection method may be applicable so far as it is detachable and allows the air-tightness to be retained, including a tapering without threading.

Further, to prevent a damage to blood cell by a projection within the containers, the inner surfaces of the containers including said blood cell collection container 5, said blood collection container portion 8 or the likes may be coated with heparin or the likes.

Still further, it is needless to say that the materials of said main container body 2, said blood plasma collection container 4, said blood cell collection container 5, said push-in cap 6, said piston 26 and the likes are not limited to those described above.

Yet further, although in the embodiment described above, the description has been made on the case where the self-blood collection is employed, it is needless to say that the present invention is applicable to the case where the normal blood collection is employed.

An aqueous solution to be used for the present invention is not limited to special ones but may include, for example, a deionized water, a distilled water and a buffer solution, and preferably it may be the buffer solution. A buffer to be used for the buffer solution may be any buffer so far as it has buffer capacity, and it may include, for example, Good buffer of pH 1 to 11, such as a lactic acid buffer, a citric acid buffer, an acetic acid buffer, a succinic acid buffer, a phthalic acid buffer, a phosphoric acid buffer, a triethanolamine buffer, a diethanolamine buffer, a lysine buffer, a barbiturate buffer, tris (hydroxymethyl) aminomethane buffer, an imidazole buffer, a malic acid buffer, an oxalic acid buffer, a glycine buffer, a boric acid buffer, a carbonic acid buffer, a glycine buffer, 3-morpholino-propanoic acid (MOPS), 1,4-piperazinebis (ethanoic sulfonic acid) (PIPES), 2-[4-(2-hydroxyethyl)-1-piperadinyl] ethanoic sulfonic acid (HEPES). A concentration of the buffer solution is not specifically limited to some values, but it may preferably within a range of 0.1 to 1000 mmol/L, more preferably 1 to 500 mmol/L.

Further, the buffer solution may, if desired, contain a surface active agent, an antiseptic agent or the like. The surface active agent may include, for example, a cationic surface active agent, an anionic surface active agent, an ampholytic surface active agent, or a nonionic surface active agent. The antiseptic agent may include, for example, a sodium azide, an antibiotic agent or the like.

When the whole blood is used as the biological sample, the aqueous solution is preferably prepared to be an isotonic solution by using salts, sugars, buffer solution or the like which has no effect on a quantification of elements to be quantified in order to prevent a variation of the concentration of element in a blood serum possibly caused by an expansion or a contraction of a blood cell such as a red blood cell or the like.

As for the kind of salts, there is no specific limitation, but it may include alkali metal halide such as sodium chloride, potassium chloride or the like. As for the kind of sugars, there is no specific limitation, but it may include sugar alcohol such as mannitol, sorbitol or the like. As for the kind of buffer solutions, those described above may be included therein.

An indicating material to be used for the present invention may be any material so far as it is neither an element to be quantified in the biological sample nor an element contained in the biological sample, and preferably it may be the element which would have no effect on the element to be quantified in the biological sample. The indicating material may be, for example, a pigment, a chromogen, a fluorescent material, a light emitting material or the like, and preferably a pigment or a chromogen. The pigment is preferable because the concentration thereof may be quantified directly by a colorimetric method.

The pigment may include, for example, an acid yellow 3, an acid yellow 23, an acid yellow 25, an acid yellow 36, an acid orange 5, an acid orange 6, an acid orange 7, an acid orange 10, an acid orange 19, an acid orange 52, an acid green 16, an acid green 25, an acid violet 43, an acid blue 3, an acid blue 9 (a brilliant blue FCF), an acid blue 40, an acid blue 45, an acid blue 47, an acid blue 59, an acid blue 74, an acid blue 113, an acid blue 158, an acid red 1, an acid red 2, an acid red 14, an acid red 18, an acid red 27, an acid red 37, an acid red 51, an acid red 52, an acid red 87, an acid red 88, an acid red 92, an acid red 94, an acid red 95, an acid red 111, a food red 17, a food yellow 3, a basic yellow 1, a basic yellow 2, a basic yellow 11, a basic orange 1, a basic orange 22, a basic green 4 (a malachite green), a basic violet 3, a basic violet 4, a basic violet 10, a basic blue 1, a basic blue 3, a basic blue 9, a basic blue 24, a basic red 1, a basic red 2, a basic red 5, a basic red 9, and a basic red 18.

As for a reductive coloring type chromogen, there may be included therein, for example, a 3-(4,5-dimethyl-2-thiazolyl)-2,5-diphenyl-2H-tetrazolium bromide (MTT), 2-(4-iodephenyl)-3-(nitrophenyl)-5-(2,4-disulfophenyl)-2H-tetrazolium monosodium salt (WST-1), 2-(4-iodephenyl)-3-(2,4-dinitrophenyl)-5-(2,4-disulfophenyl)-2H-tetra-zolium monosodium salt (WST-3) or the like.

As for an oxidative coloring type chromogen, there may be included therein, for example, a chromogen which is converted into a pigment by itself under a coexistence with an active material of peroxide such as hydrogen peroxide and peroxidase (hereafter, referred to as a leuco type chromogen), and another chromogen which generate a pigment through an oxidative coupling of two compounds (hereafter, referred to as a coupling type chromogen).

The leuco type chromogen may include, for example, 10-N-carboxymethyl carbamoyl-3,7-bis(dimethylamino)-10H-phenothiazine (CCAP), 10-N-methylcarbamoyl-3,7-bis(dimethylamino)-10H-phenothiazine (MCDP), N-(carboxymethyl aminocarbonyl)-4,4'-bis(dimethylamino) diphenylamine sodium salt (DA-64), 4,4'-bis (dimethylamino) diphenylamine, bis[3-bis(4-chlorophenyl)methyl-4-dimethylaminophenyl]amine (BCMA) or the like.

The coupling type chromogen may include, for example, a combination of a coupler such as 4-aminoantipyrine (4-AA), 3-methyl-2-benzothiazoline hydrazine or the like, and aniline such as N-ethyl-N-(3-methylphenyl)-N'succinyl ethylenediamine (EMSE), N-(3,5-dimethoxyphenyl)-N'succinyl ethylenediamine sodium salt (DOSE), N-ethyl-N-(2-hydroxy-3-sulfopropyl)-m-toluidine, N-ethyl-N-sulfopropyl-aniline, N-ethyl-N-sulfopropyl-3,5-dimethoxy-aniline, N-sulfopropyl-3,5-dimethoxy-aniline, N-ethyl-N-sulfopropyl-3,5-dimethyl-aniline, N-ethyl-N-sulfopropyl-m-toluidine, N-ethyl-N-(2-hydroxy-3-sulfopropyl)-m-anisidine, N-ethyl-N-(2-hydroxy-3-sulfopropyl) aniline, N-ethyl-N-(2-hydroxy-3-sulfopropyl)-3-methylaniline sodium salt 2 hydrate (TOOS), N-ethyl-N-(2-hydroxy-3-sulfopropyl)-3,5-dimethoxyaniline, N-(2-hydroxy-3-sulfopropyl)-3,5-dimethoxyaniline sodium salt (HSDA), N-ethyl-N-(2-hydroxy-3-sulfopropyl)-3,5-dimethylaniline, N-sulfopropyl-aniline, N-ethyl-N-sulfopropyl-anilinepropyl-m-anisidine, N-ethyl-N-(2-hydroxy-3-sulfopropyl)-4-fluoro-3,5-dimethoxy-aniline sodium salt (F-DAOS) or the like, or another combination of 4-AA and phenol or phenol such as 3-hydroxy-2,4,6-triiodo-acetic acid or the like.

The fluorescent material may include p-hydroxy phenyl-acetic acid, p-hydroxy phenyl-propionic acid, coumarin or the like.

The light emitting material may include a compound such as luminol, isoluminol, lucigenin, acridiniumester or the like.

The biological sample to be used in the present invention may be any sample including, for example, a whole blood, a blood plasma, a blood serum, a cerebrospinal fluid, a saliva, a urine, a sweat or the like, and it is preferable to use a whole blood, a blood plasma, or a blood serum therefor.

Further, the biological sample may be taken from any organism, which is not limited to a human being but may be an animal, a fish, a bird or the like. The animal may include a horse, a cattle, a pig, a wild bore, a sheep, a rabbit, a raccoon, a fox, a dog, a cat, a bear, a panda or the like, and the fish may include a conger, an ayu, a sardine, a char, an eel, a bonito, a sillaginoid, a salmon, a mackerel, a young yellowtail, a blowfish, a tuna or the like, and the bird may include a chicken, a dove or the like.

The sample for quantification used in the present invention is a solution composed of a specified volume of aqueous solution containing a specified amount of indicating material and an unknown volume of biological sample. In this sample for quantification, said aqueous solution containing a specified amount of indicating material used to dissolve the unknown volume of biological sample thereinto will be hereafter referred to as a reference solution.

The sample for quantification may be prepared either by mixing an unknown volume of biological sample collected without quantifying a volume thereof with a specified volume of aqueous solution containing a specified amount of indicating material, or by adding a specified volume of aqueous solution containing a specified amount of chromogen to a solution made by mixing an unknown volume of biological sample and a specified volume of aqueous solution. Accordingly, since there is no need to use a container for quantifying a volume of the biological sample, the sample for quantification can be easily prepared right on the spot of collection of the biological sample. Further, very small amount of biological sample may be sufficient to prepare the sample for quantification.

The reference solution may be prepared either by mixing a specified amount of indicating material with a specified volume of aqueous solution or by adding a specified volume of aqueous solution containing a specified amount of chromogen to a specified volume of aqueous solution.

The biological sample may be obtained by a normal method without using a specific one, that is, for example, the blood serum may be obtained from the whole blood by, after having left it for a while, applying a centrifugal processing thereto, and the blood plasma may be obtained by treating the whole blood with a separation processing such as a membrane separation.

In the present invention, a self-blood collection method where, for example, a test subject collects his/her blood in person by manipulating a blood collecting needle may be used preferably. In addition, since this operation may be performed without quantifying a volume thereof and accordingly no special technique is required for preparing the sample for quantification, the test subject can prepare the sample for quantification by himself/herself. Further, the sample for quantification prepared by mixing the whole blood directly with a specified volume of aqueous solution can be used as a sample for determining a concentration of the elements to be quantified in the blood plasma or the blood serum from a value obtained by quantifying the elements to be quantified in the sample for quantification after, if necessary, having separated blood cell element by the separation processing such as a centrifugal separation and a membrane separation and a dilution ratio determined based on a dilution ratio calculation method described below.

There is no special limitation on a manner for mixing the biological sample with the specified volume of aqueous solution, but the sample obtained in the above-described method may be added directly or may be added indirectly through a separation device installed in a container. The latter adding method may include, for example, a method where by using the blood separation instrument of the present invention, the blood plasma separated from the whole blood is added.

There is no special limitation on a range of the dilution ratio of the indicating material in the sample for quantification, but it is preferably 2 to 10, more preferably 2 to 50, and most preferably 2 to 20.

It is to be noted that if the specified volume of aqueous solution does not contain a specified amount of indicating material, after the biological sample having been mixed therewith, a specified volume of aqueous solution containing a specified amount of indicating material may be added thereto.

A process for quantifying the elements to be quantified in an unknown volume of biological sample comprises the steps of quantifying a concentration of the indicating material in a reference solution and a concentration of the indicating material in the sample for quantification to determine the dilution ratio of the biological sample, and quantifying a concentration of the elements to be quantified in the sample for quantification.

The concentration (X) of the elements to be quantified in the biological sample may be determined by an equation 1 as a function of the concentration (Y) of the elements to be quantified in the sample for quantification prepared by the above-described method and the dilution ratio (a) of the biological sample in the sample for quantification.

$$X = aY \quad \text{(eq. 1)}$$

In the present invention, the dilution ratio can be determined as described below.

$$C_2 = M_1/(V_1+V_2) \quad \text{(eq. 2)}$$

where, $C_2$ is the concentration of the indicating material in the sample for quantification, $V_1$ is the volume of the aqueous solution used for preparing the sample for quantification, $M_1$ is the amount of the indication material used therefor, and $V_2$ is the volume of the biological sample used therefor (note: $V_2$ is not measured).

On the other hand, the concentration $C_1$ of the indicating material in the aqueous solution (=the reference solution) used for preparing the sample for quantification can be represented as:

$$C_1 = M_1/V_1 \quad \text{(eq. 3)}$$

It is to be noted that in the method for preparing the sample for quantification from the biological sample, the reference solution is a solution prepared without using the biological sample.

Since the dilution ratio (a) of the unknown volume of biological sample in the sample for quantification can be represented as:

$$a = (V_1+V_2)/V_2 \quad \text{(eq. 4)}$$

the dilution ratio (a) may be rewritten by using $C_1$ and $C_2$ as shown in equation 5.

$$\text{Dilution ratio } (a) = (V_1+V_2)/V_2 = C_1/(C_1-C_2) \quad \text{(eq. 5)}$$

Herein, the concentrations $C_1$ and $C_2$ of the indicating material can be determined by measuring an absorptivity when the indicating material is a pigment or a chromogen, by measuring a light emitting intensity when the indicating material is a light emitting material, or by measuring a fluorescence intensity when the indicating material is a fluorescent material. When the indicating material is quantified by the absorptivity, since the concentration is in proportion to the absorptivity, they may be written as:

$$C_2/C_1 = E_2/E_1 \quad \text{(eq. 6)}$$

where, $C_1$ and $E_1$ are the concentration and the absorptivity of the reference solution, and $C_2$ and $E_2$ are those of the sample for quantification, respectively. Accordingly, the dilution ratio can be determined also by an equation rewritten as:

$$\text{Dilution ratio } (a) = C_1/(C_1-C_2) = E_1/(E_1-E_2) \quad \text{(eq. 7)}$$

As having been described above, the dilution ratio can be calculated based on the $C_1$ and $C_2$ values or the $E_1$ and $E_2$ values. It is to be noted that although the $C_1$ or the $E_1$ value may be set in advance to a known value, since they may be quantified by using the newly prepared solution, the amount of the indicating material in the reference solution may not be set in advance to a known value. That is, in the present invention, a volume of a solution to be mixed directly with the biological sample, and if this solution contains the indicating material, an amount or a concentration of the indicating material and a volume of the solution containing the indicating material and an amount or a concentration of the indicating material used for preparing the sample for quantification, each of them may not be known but arbitrary so far as it is constant.

The method for quantifying the indicating material may be any method so far as it can quantify the concentration of the indicating material. When the indicating material is a pigment, the absorptivity of the sample for quantification itself can be quantified. Further, in other cases, a specified volume of sample is taken out of the sample for quantification and then the concentration thereof is quantified by a quantifying method for the indicating material to be quantified. Upon quantification, when the absorptivity is used therefor, the value of absorptivity can be used directly without converting it to the concentration of the indicating material.

In the present invention, any one of a colorimetric method, a light emitting method and a fluorometric method may be used, and among them, the colorimetric method is most preferable.

The indicating material to be used in the colorimetric method may include, for example, the above-described pigments and chromogens. The chromogens may include the reductive coloring type chromogen and the oxidative coloring type chromogen. The colorimetric method using the reductive coloring type chromogen may include a method in which the reductive coloring type chromogen is converted into the pigment by an operation of an electron carrier of a reductive coenzyme such as NAD(P)H or the like, dihydrolipoamide dehydrogenase, 1-methoxy-5-methylphenaziummethylsulfate or the like and then the absorptivity of the generated pigment is measured by a spectrophotometer. The colori-metric method using the oxidative coloring type chromogen may include a method in which the oxidative coloring type chromogen is converted into the pigment by an operation of active material of peroxide such as hydrogen peroxide, peroxidase or the like and then the absorptivity of the generated pigment is measured by the spectrophotometer. In the case where the chromogen is used, the method using the oxidative coloring type chromogen is preferable.

When the chromogen is used as the indicating material, the chromogen is converted into the pigment by the method described below and then the absorptivity of the generated pigment is measured. In the case where the reductive coloring type chromogen is used, the reductive coloring type chromogen is converted into the pigment by the operation of the electron carrier of the reductive coenzyme such as NAD(P)H or the like, dihydrolipoamide dehydrogenase, 1-methoxy-5-methylphenaziummethylsulfate or the like and then the absorptivity of the generated pigment is measured. In the case where the oxidative coloring type chromogen is used, the oxidative coloring type chromogen is converted into the pigment by the operation of the active material of peroxide such as hydrogen peroxide, peroxidase or the like and then the absorptivity of the generated pigment is measured.

The fluorometric method may include a method in which the fluorescence emitted from the above-described fluorescent material by the active material of peroxide such as hydrogen peroxide, peroxidase or the like is measured by a fluorophotometer.

The fluorometric method may further include another method in which the light (photon) emitted from the above-described fluorescent material by the active material of peroxide such as hydrogen peroxide, peroxidase or the like is measured by a luminometer.

It is to be noted that in the case where the coupling type chromogen is used as the oxidative coloring type chromogen, either one of two compounds pertaining to the color development as the indicating material in the sample for quantification is contained and the other compound is preserved separately.

When the oxidative coloring type chromogen is used as the indicating material, a mole-number of this oxidative coloring type chromogen should be controlled to be less than that of the hydrogen peroxide. When the coupling type chromogen is used as the indicating material, the mole-number of this chromogen should be controlled to be less than that of each of the hydrogen peroxide and said the other compound.

The hydrogen peroxide to be used for converting the oxidative coloring type chromogen into the pigment may be hydrogen peroxide itself and it may be generated directly or indirectly from other materials by using enzyme as well. A combination of the material and the enzyme for generating hydrogen peroxide directly or indirectly may include such ones as: cholesterol and cholesterol oxidase; uric acid and uricase; triglyceride and lipoprotein lipase & glycerol oxidase; free fatty acid and acyl-CoA synthetase & acyl-CoA oxidase; glucose and pyranose oxidase; phospholipid and phospholipase D & choline oxidase; creatine and creatinase & sarcosine oxidase; creatinine and creatininase, creatinase & sarcosine oxidase; lactic acid and lactose oxidase; inorganic phosphorous and purine nucleotide phosphorylase & xanthine oxidase; 2,4-dimethoxy-benzoyl-choline and cholinesterase & choline oxidase; allyllamine and monoamine oxidase; and so on.

A reagent chemical for converting the oxidative coloring type chromogen as the indicating material in the sample for quantification into the pigment may be preserved as a single-reagent system or as a plural-reagent system. A preservation as the plural-reagent system is preferable and that as two-reagent system is more preferable. In the case where hydrogen peroxide itself is used, the two-reagent system is preferable which avoids a coexistence of hydrogen peroxide and the active material of peroxide such as peroxidase. In the case where hydrogen peroxide is generated directly or indirectly from other materials by using enzyme, the two-reagent system is preferable which avoids a coexistence of the enzyme to be reacted with the material directly and the material itself. Preferred embodiments of preserving manners of the reagent chemical for converting the oxidative coloring type chromogen into the pigment will be described below. However, it is to be apprehended that the preserving manner is not limited to those embodiments below.

The chromogen in the sample for quantification: N-(2-hydroxy-3-sulfopropyl)-3,5-dimethoxyaniline sodium salt (HSDA)

A first reagent: A reagent prepared by subtracting HSDA from a first reagent of Determiner GL-E (reagent for measuring glucose: provided by Kyowa-medex Corp.) plus glucose.

A second reagent: A second reagent of Determiner GL-E

There is no special limitation on the element to be quantified, but the elements in the blood serum may be preferably included therein. Further, although the quantifying operation of the elements to be quantified is not limited to special manner but can be performed by a general method established as a quantifying method for the elements to be quantified, such a quantifying method is preferable that is not affected substantially by the indicating material.

The elements to be quantified and an example of the measuring method therefor will be described below with the latter indicated in parenthesis. Total protein (biuret method), GOT (JSCC method), GPT (JSCC method), L-lactate dehydro-genase (SSCC method), γ-GTP (JSCC method), creatinine kinase (IFCC method), cholinesterase (p-HBC method), HDL cholesterol (enzyme method), LDL cholesterol (enzyme method), triglyceride (enzyme method), urea nitrogen (enzyme method), creatinine (enzyme method), uric acid (enzyme method), glucose (enzyme method), alkaline phosphatase (GSCC method), ammonium (enzyme method), sialic acid (enzyme method), ceruloplasmin (colorimetric method), free cholesterol (enzyme method), free fatty acid (enzyme method), lactic acid (enzyme method), lipase (enzyme method), inorganic phosphorus (enzyme method), and monoamine oxidase (enzyme method).

A container equipped with a closable opening/closing device for adding the biological sample thereinto with a specified volume of above-described aqueous solution precisely contained therein is used as the container for collecting and preserving the biological sample or for preparing the sample for quantification. Thus, the test subject can add a proper volume of biological sample such as his/her blood collected by himself/herself without any help of the specifically qualified person such as the doctor, the nurse and the clinical inspection engineer or the expert engineer, without any treatment, for example, as the whole blood and without quantifying the volume thereof one by one, to the container with the specified volume of aqueous solution filled therein, and after having applied thereto a device for preventing a possible vaporization and leakage of the solution contained therein, send to the proper organization (inspection center or hospital) to ask said organization the quantification of the elements which he/she wants to be quantified.

Figure 27:
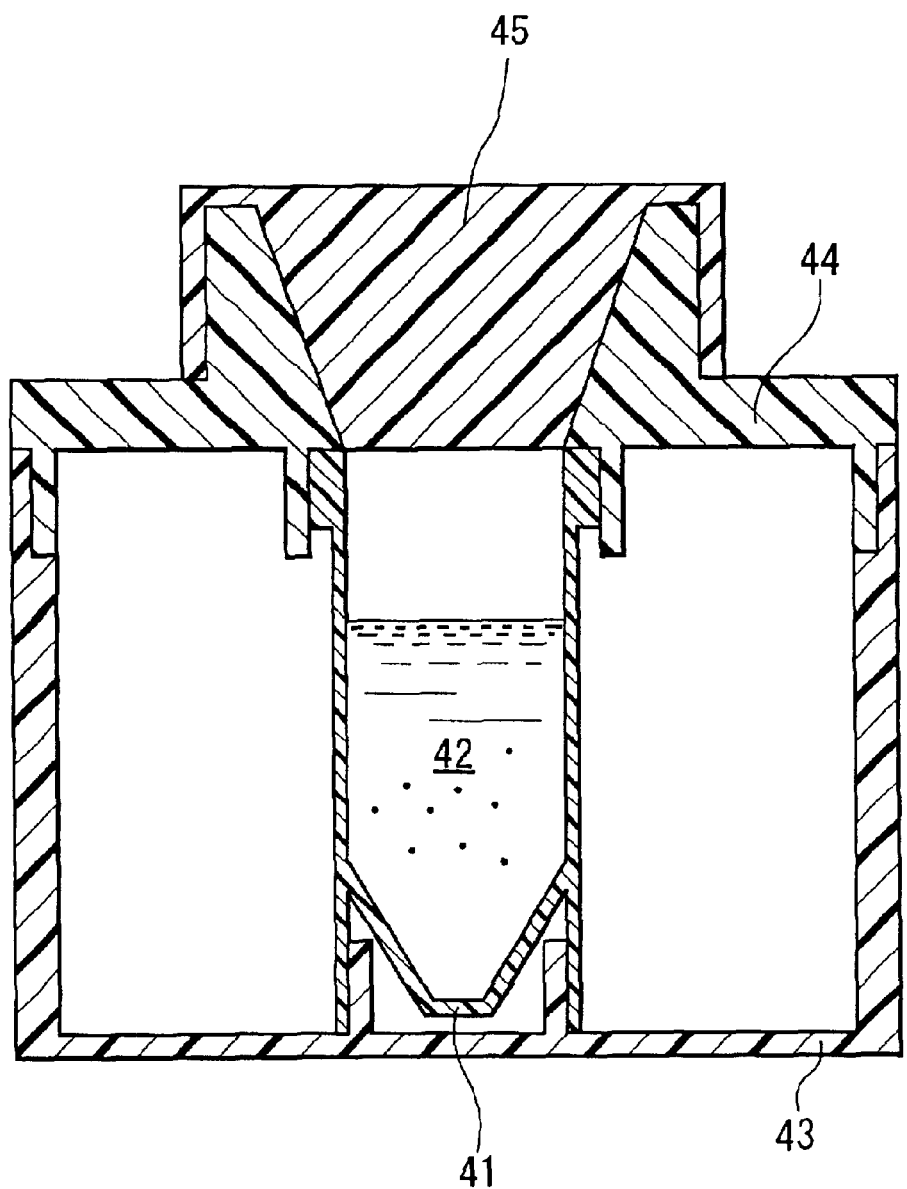
FIG. 27 is a cross sectional view of an embodiment of the present invention.

There is no special limitation on the container so far as it has a closable opening/closing device capable of preventing vaporization and leakage of the aqueous solution, and, for example, a reagent bottle with screw cap may be suitable therefor. A preferred embodiment of such container is shown in FIG. 1 previously referred thereto, and a simpler one is shown in FIG. 27. FIG. 27 shows a container for preserving the biological sample or for preparing the sample for quantification according to the present invention, which is equipped with a closable opening/closing device for adding the biological sample thereinto. The container according to the present invention will now be described below.

This container comprises a container 41 for collecting a biological sample into which the biological sample is to be added actually, a housing container 43 for receiving the container for collecting the biological sample, said housing container 43 being detachable and being used for stably holding said container 41 for collecting the biological sample, an inner cap 44 for stably fixing said housing container 43 for receiving the container for collecting the biological sample, and an outer cap 45 for stably fixing said container 41 for collecting the biological sample and said inner cap 44. The container 41 for collecting the biological sample contains a specified volume of aqueous solution 42. Further, a specified amount of indicating material is contained in said aqueous solution 42. Thus, the container 41 for collecting the biological sample can be used also as a container for preparing the sample for quantification. The container 41 for collecting the biological sample has no special limitation on a shape thereof, but preferably it may have a shape allowing it to be mounted directly on a turn table of an automatic analyzer. The housing container 43 for receiving the container for collecting the biological sample fixedly holds the container 41 for collecting the biological sample to prevent a falling of the container 41 and a leakage of the aqueous solution 42 possibly caused thereby. Accordingly, the housing container 43 is preferably configured into a shape having both a portion for receiving the container 41 and a portion for securing a positional stability of the whole container. The inner cap 44 and the outer cap 45 serve to close the container 41 and the housing container 43 and thereby confine the aqueous solution 42 in the container 41 for collecting the biological sample thereinto. The inner cap 44 is preferably configured into a shape having a function to fit tightly with each of the housing container 43 and the outer cap 45. The outer cap 45 is preferably configured into a shape having an opening/closing function and also having a portion to fit with the inner cap 44 tightly and a portion to close the container 41 thereby preventing the vaporization and the leakage of the solution 42. It is to be noted that the volume of the aqueous solution 42 to be contained in the container 41 is not limited to the special value, but preferably it is 100 to 5000 $\mu$L and more preferably 200 to 2000 $\mu$L.

Some examples of experiment according to the present invention will now be shown below, but it is to be apprehended that the present invention does not limited to those examples. The reagents and the enzymes used for the experiments are shown below:

Reagent for quantifying glucose: Determiner GL-E (Kyowa-medex Corp.), Glucose reference solution (200 mg/dL, A&T Corp.), Isotonic sodium chloride solution (0.9%, prepared in the laboratory), and Ion exchange water (2 $\mu$S/cm or lower, Organo Corp.)

EMBODIMENTS

Embodiment No. 1
Dilution Ratio Calculation of the Blood Serum in the Case Where HSDA is Used as the Indicating Material Eleven pieces of test tubes (diameter: 10 mm; length: 73 mm) were prepared, and a 1000 $\mu$L of aqueous solution containing HSDA prepared by double-diluting the reagent 1-B of Determiner GL-E with the ion exchange water was precisely divided and poured into respective test tubes. Then a human pooled serum (prepared from ten person's serum through 3000 rpm centrifugal separation processing to be pooled and preserved) was, as shown in Table 1, precisely divided by a unit of 10 $\mu$L and poured into the test tubes Nos. 1 to 11. After having been poured into respective test tubes, they were stirred for five minutes by a mixer (AUTOMATIC LAB MIXER MODEL TH-2).

TABLE 1

| Test tube No. | Added human serum ($\mu$L) | Theoretical dilution ratio |
|---|---|---|
| 1 | 10 | 101.0 |
| 2 | 20 | 51.0 |
| 3 | 40 | 26.0 |
| 4 | 60 | 17.7 |
| 5 | 80 | 13.5 |
| 6 | 100 | 11.0 |
| 7 | 120 | 9.3 |
| 8 | 140 | 8.1 |
| 9 | 160 | 7.3 |
| 10 | 180 | 6.6 |
| 11 | 200 | 6.0 |

HSDA in the aqueous solution containing HSDA and HSD in the eleven samples described in Table 1 were guided to a pigment by using Determiner GL-E, and the absorptivity thereof was measured. In specific, the aqueous solution containing HSDA and each of the eleven samples (5 $\mu$L) described in Table 1 were mixed with 40 mg/dL glucose aqueous solution (50 $\mu$L) and warmed at 37° C. for five minutes, and then, to this mixture was added the reagent (50 $\mu$L) prepared by adding the whole amount of reagent 2-B (enzyme agent dissolving liquid) of Determiner GL-E to the reagent 2-A (enzyme agent) of the same, and further, the mixture was warmed at 37° C. for five minutes, and after that the absorptivity of the generated pigment was measured at a dominant wavelength of 596 nm and at a sub-wavelength of 884 nm by an automatic analyzer Bio Majesty JCA-BA1650 (provided by JEOL Corp.). The absorptivity $E_1$ in the case of the aqueous solution containing HSDA being used was 0.4486 (=4486×10$^{-4}$), and the absorptivity of the samples Nos. 1 to 11 was such as shown in Table 2.

The dilution ratio [=$E_1/(E_1-E_2)$] was calculated based on the $E_1$ value and the respective $E_2$ values and compared with the theoretical dilution ratio. The result thereof is shown in Table 2.

value and the $E_2$ value. Further, the total protein (TP) in the sample for quantification of the test tubes Nos. 1 to 10 was quantified by the biuret method. Further, the human's serum value was calculated based on the dilution ratio and the total protein (TP) value for each test sample, and the coincidence rate with the total protein (TP) value calculated by using the blood serum was determined. It is to be noted that the $E_1$ value (the value multiplied by $10^4$) was 870 and the total protein (TP) value quantified by using the blood serum directly was 6.9 g/dL. The result is shown in Table 3.

TABLE 2

| Test tube No. | Theoretical dilution ratio | $E_2$ (×$10^4$) | $E_1 - E_2$ (×$10^4$) | Calculated dilution ratio | Coincidence rate (%) |
|---|---|---|---|---|---|
| 1 | 101.0 | 4455 | 31 | 144.7 | 143.3 |
| 2 | 51.0 | 4397 | 89 | 50.4 | 98.8 |
| 3 | 26.0 | 4314 | 172 | 26.1 | 100.3 |
| 4 | 17.7 | 4243 | 243 | 18.5 | 104.5 |
| 5 | 13.5 | 4162 | 324 | 13.8 | 102.6 |
| 6 | 11.0 | 4101 | 385 | 11.7 | 105.9 |

TABLE 2-continued

| Test tube No. | Theoretical dilution ratio | $E_2$ (×$10^4$) | $E_1 - E_2$ (×$10^4$) | Calculated dilution ratio | Coincidence rate (%) |
|---|---|---|---|---|---|
| 7 | 9.3 | 4012 | 474 | 9.5 | 101.4 |
| 8 | 8.1 | 3949 | 537 | 8.4 | 102.6 |
| 9 | 7.3 | 3858 | 628 | 7.1 | 98.5 |
| 10 | 6.6 | 3803 | 683 | 6.6 | 100.2 |
| 11 | 6.0 | 3747 | 739 | 6.1 | 101.2 |

Thus, with an exception of the test tube No. 1, the calculated dilution ratio well coincides with the theoretical dilution ratio within the range of the theoretical dilution ratio of 6.0 to 51.0.

Embodiment No. 2
Quantification of Total Protein (TP) in the Diluted Blood Serum by the Biuret Method The dilution ratio of the blood serum using the acid blue 9 (brilliant blue FCF) as the indicating material was calculated, and the total protein (TP) in said diluted blood serum was quantified by the biuret method to quantify the total protein (TP) in said blood serum.

HEPES buffer solution (pH 7.7) of 0.1 mol/L concentration containing the acid blue 9 (brilliant blue FCF) was prepared as the aqueous solution containing the indicating material. This solution was divided and poured into ten test tubes by precisely 1000 μL for each test tube. Then, the human's blood serum was added to respective test tubes by at first 50 μL then increasing by 50 μL for each test tube as shown in Table 3 to prepare Nos. 1 to 10 samples for quantification.

The absorptivity ($E_1$) of the HEPES buffer solution containing the acid blue 9 before adding the blood serum thereto and the absorptivity ($E_2$) of the sample for quantification with the blood serum having added thereto were measured at 630 nm. The dilution ratio was calculated based on the $E_1$

TABLE 3

| Test tube No. | Added serum (μL) | $E_2$ (×$10^4$) | Theoretical dilution ratio | Calculated dilution ratio | Measured concentration (g/dL) | Calculated concentration (g/dL) | Coincidence rate (%) |
|---|---|---|---|---|---|---|---|
| 1 | 50 | 817 | 21.0 | 16.4 | 0.4 | 6.6 | 95.2 |
| 2 | 100 | 784 | 11.0 | 10.1 | 0.7 | 7.1 | 102.6 |
| 3 | 150 | 756 | 7.7 | 7.6 | 0.9 | 6.9 | 99.5 |
| 4 | 200 | 724 | 6.0 | 6.0 | 1.2 | 7.2 | 103.6 |
| 5 | 250 | 699 | 5.0 | 5.1 | 1.5 | 7.6 | 110.6 |
| 6 | 300 | 671 | 4.3 | 4.4 | 1.6 | 7.0 | 101.4 |
| 7 | 350 | 647 | 3.9 | 3.9 | 1.8 | 7.0 | 101.8 |
| 8 | 400 | 624 | 3.5 | 3.5 | 2.0 | 7.1 | 102.5 |
| 9 | 450 | 605 | 3.2 | 3.3 | 2.2 | 7.2 | 104.7 |
| 10 | 500 | 594 | 3.0 | 3.2 | 2.3 | 7.3 | 105.1 |

Thus, because of good coincidence rate for every sample, it has been ascertained that the quantification of the total protein (TP) in the biological sample obtained by using this quantifying method is effective for every dilution ratio within its range of 3 to 21.

Embodiment No. 3

Quantification of the GOT in the Diluted Blood Serum by the JSCC Method

The GOT in the ten samples of diluted blood serum with various dilution ratios prepared according to the method described in the Embodiment No. 2 was quantified by the JSCC method. It is to be noted that the $E_1$ value (the value multiplied by $10^4$) was 870 and the GOT quantified by using the blood serum directly was 48U/L. The result is shown in Table 4.

TABLE 4

| Test tube No. | Added serum (μL) | $E_2$ (×10$^4$) | Theoretical dilution ratio | Calculated dilution ratio | Measured concentration (U/dL) | Calculated concentration (U/dL) | Coincidence rate (%) |
|---|---|---|---|---|---|---|---|
| 1 | 50 | 817 | 21.0 | 16.4 | 4 | 66 | 136.8 |
| 2 | 100 | 784 | 11.0 | 10.1 | 5 | 51 | 105.4 |
| 3 | 150 | 756 | 7.7 | 7.6 | 6 | 46 | 95.4 |
| 4 | 200 | 724 | 6.0 | 6.0 | 8 | 48 | 99.3 |
| 5 | 250 | 699 | 5.0 | 5.1 | 12 | 61 | 127.2 |
| 6 | 300 | 671 | 4.3 | 4.4 | 13 | 57 | 118.4 |
| 7 | 350 | 647 | 3.9 | 3.9 | 13 | 51 | 105.7 |
| 8 | 400 | 624 | 3.5 | 3.5 | 14 | 50 | 103.2 |
| 9 | 450 | 605 | 3.2 | 3.3 | 14 | 46 | 95.8 |
| 10 | 500 | 594 | 3.0 | 3.2 | 16 | 50 | 105.1 |

Thus, with an exception of the test tube No. 1, good coincidence rate has been observed. Accordingly, it has been ascertained that the quantification of the GOT in the biological sample obtained by using this quantifying method is effective for every dilution ratio within its range of 3 to 11.

Embodiment No. 4
Quantification of the Uric Acid in the Diluted Blood Serum by the Enzyme Method The uric acid in the ten samples of diluted blood serum with various dilution ratios prepared according to the method described in the Embodiment No. 2 was quantified by the enzyme method, that is, after the uric acid had been converted into allantoin and hydrogen peroxide by uricase, the generated hydrogen peroxide was guided to the pigment by peroxidase, 4-aminoantipyrine and F-DAOS to quantify the uric acid in each sample. It is to be noted that the $E_1$ value (the value multiplied by $10^4$) was 870 and the uric acid value quantified by using the blood serum directly was 4.8 mg/dL. The result is shown in Table 5.

Thus, with an exception of the test tube No. 1, good coincidence rate has been observed. Accordingly, it has been ascertained that the quantification of the uric acid in the biological sample obtained by using this quantifying method is effective for every dilution ratio within its range of 3 to 11.

Embodiment No. 5
Quantification of the Total Cholesterol in the Diluted Blood Serum by the Enzyme Method The total cholesterol in the ten samples of diluted blood serum with various dilution ratios prepared according to the method described in the Embodiment No. 2 was quantified by the enzyme method. That is, after the ester type cholesterol had been hydrolyzed by chemically modified cholesterol esterase, the free cholesterol in the reaction system was converted into cholestenone and hydrogen peroxide by cholesterol oxidase, and then the generated hydrogen peroxide was guided to the pigment by peroxidase, 4-aminoantipyrine and DOSE to quantify the total cholesterol in each sample. It is to be noted that the $E_1$ value (the

TABLE 5

| Test tube No. | Added serum (μL) | $E_2$ (×10$^4$) | Theoretical dilution ratio | Calculated dilution ratio | Measured concentration (mg/dL) | Calculated concentration (mg/dL) | Coincidence rate (%) |
|---|---|---|---|---|---|---|---|
| 1 | 50 | 817 | 21.0 | 16.4 | 0.2 | 3.3 | 68.4 |
| 2 | 100 | 784 | 11.0 | 10.1 | 0.5 | 5.1 | 105.4 |
| 3 | 150 | 756 | 7.7 | 7.6 | 0.6 | 4.6 | 95.4 |
| 4 | 200 | 724 | 6.0 | 6.0 | 0.8 | 4.8 | 99.3 |
| 5 | 250 | 699 | 5.0 | 5.1 | 0.9 | 4.6 | 95.4 |
| 6 | 300 | 671 | 4.3 | 4.4 | 1.1 | 4.8 | 100.2 |
| 7 | 350 | 647 | 3.9 | 3.9 | 1.2 | 4.7 | 97.5 |
| 8 | 400 | 624 | 3.5 | 3.5 | 1.4 | 5.0 | 103.2 |
| 9 | 450 | 605 | 3.2 | 3.3 | 1.5 | 4.9 | 102.6 |
| 10 | 500 | 594 | 3.0 | 3.2 | 1.6 | 5.0 | 105.1 | value multiplied by $10^4$) was 870 and the total cholesterol value quantified by using the blood serum directly was 137 mg/dL. The result is shown in Table 6.

TABLE 6

| Test tube No. | Added serum (μL) | $E_2$ (×10$^4$) | Theoretical dilution ratio | Calculated dilution ratio | Measured concentration (mg/dL) | Calculated concentration (mg/dL) | Coincidence rate (%) |
|---|---|---|---|---|---|---|---|
| 1 | 50 | 817 | 21.0 | 16.4 | 6 | 98 | 71.9 |
| 2 | 100 | 784 | 11.0 | 10.1 | 12 | 121 | 88.6 |
| 3 | 150 | 756 | 7.7 | 7.6 | 18 | 137 | 100.3 |
| 4 | 200 | 724 | 6.0 | 6.0 | 23 | 137 | 100.0 |
| 5 | 250 | 699 | 5.0 | 5.1 | 28 | 142 | 104.0 |

TABLE 6-continued

| Test tube No. | Added serum ($\mu$L) | $E_2$ ($\times 10^4$) | Theoretical dilution ratio | Calculated dilution ratio | Measured concentration (mg/dL) | Calculated concentration (mg/dL) | Coincidence rate (%) |
|---|---|---|---|---|---|---|---|
| 6 | 300 | 671 | 4.3 | 4.4 | 32 | 140 | 102.1 |
| 7 | 350 | 647 | 3.9 | 3.9 | 36 | 140 | 102.5 |
| 8 | 400 | 624 | 3.5 | 3.5 | 40 | 141 | 103.3 |
| 9 | 450 | 605 | 3.2 | 3.3 | 43 | 141 | 103.0 |
| 10 | 500 | 594 | 3.0 | 3.2 | 44 | 139 | 101.2 |

Thus, with an exception of the test tube No. 1, good coincidence rate has been observed. Accordingly, it has been ascertained that the quantification of the total cholesterol in the biological sample obtained by using this quantifying method is effective for every dilution ratio within its range of 3 to 11.

Embodiment No. 6

A container which receives 1000 $\mu$L of aqueous solution with a composition described below and holds it in a sealed condition and which the test subject uses to collect his/her blood and to prepare the sample for quantification by himself/herself was manufactured as shown in FIG. 27.

Composition of the aqueous solution

| HSDA | 1.3 mmol/L |
|---|---|
| HEPES (pH 6.5) | 0.1 mol/L |

Embodiment No. 7

The container which receives 1000 $\mu$L of aqueous solution with a composition described below and holds it in a sealed condition and which the test subject uses to collect his/her blood and to prepare the sample for quantification by himself/herself was manufactured as shown in FIG. 27.

Composition of the aqueous solution

| Acid blue 9 (brilliant blue FCF) | 0.018 mmol/L |
|---|---|
| HEPES (pH 7.7) | 0.1 mol/L |
| Brij-35 (30%) | 0.29% (v/v) |

According to the present invention described above, since a separating process of blood into the blood plasma and the blood cell could be done only by applying the pressure to the collected blood, a variety of effects is advantageously provided, including that the reduction in operational cost as well as the simplification in operation could be accomplished.

Further, according to the present invention, there have been provided the method for preparing the sample for quantification from the biological sample, which is to be used for quantifying the elements to be quantified in said biological sample; the method for quantifying the elements to be quantified in the biological sample; the container for preserving the unknown volume of biological sample containing elements to be quantified, which has been collected without quantifying the volume thereof, until it will be quantified; and the container used for preparing the sample for quantification from the unknown volume of biological sample containing the elements to be quantified, which has been collected without quantifying the volume thereof.

What is claimed is:

1. A method of preparing a biological sample for quantification which includes an element to be quantified
said method comprising steps of
collecting a volume of biological sample without quantifing the volume thereof to mix with a specified volume of an aqueous solution,
measuring an absorptivity of an indicating material in the aqueous solution,
measuring an absorptivity of the indicating material in the collected biological sample mixed with the specified volume of the aqueous solution,
calculating a dilution ratio of the biological sample using the absorptivity of the indicating material in the specified volume of the aqueous solution and the absorptivity of the indicating material in said biological sample mixed with the specified volume of the aqueous solution,
measuring an absorptivity of said element in the biological sample mixed with the specified volume of aqueous solution, and;
obtaining a quantified value of said element in the biological sample using the measured absorptivity of said element and the calculated dilution ratio.

2. A method in accordance with claim 1, in which said specified volume of aqueous solution contains a specified amount of indicating material.

3. A method in accordance with claim 1, in further comprising a step of adding a specified volume of aqueous solution containing a specified amount of indicating material.

4. A method in accordance with claim 1, in which said indicating material is a pigment or a chromogen.

5. A method in accordance with claim 4, in which said chromogen is an oxidative coloring type chromogen.

6. A method in accordance with claim 1, in which said biological sample is either one of a whole blood, a blood plasma or a blood serum.

7. A method in accordance with claim 1, in which said aqueous solution is a buffer solution.

8. A method in accordance with claim 1, in which said elements to be quantified are elements in the blood serum.

* * * * *